United States Patent
Song et al.

(10) Patent No.: US 12,168,719 B2
(45) Date of Patent: Dec. 17, 2024

(54) COMPOSITION OF THERMOSENSITIVE HYDROGELS HAVING ALTERED REVERSIBLE SOL-GEL TRANSITION PROPERTY, AND USE THEREOF

(71) Applicant: Nexgel Biotech Co., Ltd, Hanam-si (KR)

(72) Inventors: Soo Chang Song, Seoul (KR); Bo-Bae Seo, Seoul (KR)

(73) Assignee: Nexgel Biotech Co. Ltd, Hanam-si (KR)

( * ) Notice: Subject to any disclaimer, the term of this patent is extended or adjusted under 35 U.S.C. 154(b) by 512 days.

(21) Appl. No.: 16/986,507

(22) Filed: Aug. 6, 2020

(65) Prior Publication Data
US 2021/0163691 A1    Jun. 3, 2021

(30) Foreign Application Priority Data
Nov. 29, 2019    (KR) .................... 10-2019-0156759

(51) Int. Cl.
| | | |
|---|---|---|
| C08G 79/025 | (2016.01) | |
| A61L 27/18 | (2006.01) | |
| A61L 27/52 | (2006.01) | |
| B33Y 70/10 | (2020.01) | |
| B33Y 80/00 | (2015.01) | |

(52) U.S. Cl.
CPC ............ *C08G 79/025* (2013.01); *A61L 27/18* (2013.01); *A61L 27/52* (2013.01); *B33Y 70/10* (2020.01); *B33Y 80/00* (2014.12); *C08G 2210/00* (2013.01)

(58) Field of Classification Search
None
See application file for complete search history.

(56) References Cited

U.S. PATENT DOCUMENTS

| | | | |
|---|---|---|---|
| 6,319,984 B1 * | 11/2001 | Song ................ | C08G 79/025 525/54.1 |
| 7,259,225 B2 | 8/2007 | Song et al. | |
| 9,526,699 B2 | 12/2016 | Song et al. | |

(Continued)

FOREIGN PATENT DOCUMENTS

| | | |
|---|---|---|
| CA | 2999351 A1 * | 10/2018 |
| CN | 1829763 A | 9/2006 |
| CN | 10-9381749 A | 2/2019 |

(Continued)

OTHER PUBLICATIONS

KR Office Action dated Nov. 18, 2020 issued in Application No. 10-2019-0156759.

(Continued)

*Primary Examiner* — Tae H Yoon
(74) *Attorney, Agent, or Firm* — Hyounggook Lee

(57) ABSTRACT

The present invention relates to a thermosensitive hydrogel composition, which while comprising an amino acid ester, polyethylene glycol, and a functional group for the introduction of a functional moiety at an end thereof at a predetermined ratio, comprises a polyphosphazene-based polymer having a controlled length and a content of polyethylene glycol contained therein, in which a reversible sol-gel transition character is altered; a medical polymer hydrogel comprising the polyphosphazene-based polymer; or an ink composition for 3D printing.

14 Claims, 10 Drawing Sheets

(56) References Cited

U.S. PATENT DOCUMENTS

2018/0133362 A1* 5/2018 Song ............... A61L 24/046

FOREIGN PATENT DOCUMENTS

| EP | 2540764 A2 | 1/2013 |
| JP | 2009531471 A | 9/2009 |
| KR | 100259367 B1 | 6/2000 |
| KR | 100315630 B1 | 12/2001 |
| KR | 20110086326 A | 7/2011 |
| KR | 101850424 B1 | 4/2018 |
| KR | 20180128227 A | 12/2018 |
| WO | 2008153277 A1 | 12/2008 |
| WO | WO 2008/153278 A1 * | 12/2008 |

OTHER PUBLICATIONS

Office Action issued in corresponding CN Patent Application No. 202080082532.8, dated Jan. 18, 2023, 16 pp.

Teasdale et al.: "Polyphosphazenes: Multifunctional, Biodegradable Vehicles for Drug and Gene Delivery", POLYMERS, vol. 5, No. 1, Feb. 8, 2013 (Feb. 8, 2013), pp. 161-187, XP055596564, DOI: 10.3390/polym5010161.

Kang et al: "Controlled release of doxorubicin from thermosensitive poly(organophosphazene) hydrogels", International Journal of Pharmaceutics, Elsevier, NL, vol. 319, No. 1-2, Aug. 17, 2006 (Aug. 17, 2006), pp. 29-36, XP027972433, ISSN: 0378-5173.

Al-Abd et al: "Pharmacokinetics of doxorubicin after intratumoral injection using a thermosensitive hydrogel in tumor-bearing mice", Journal of Controlled Release, Elsevier, Amsterdam, NL, vol. 142, No. 1, Feb. 25, 2010 (Feb. 25, 2010), pp. 101-107, XP026892479, ISSN: 0168-3659, DOI: 10.1016/J.JCONREL.2009.10.003.

Extend European Search Report dated Oct. 19, 2023 in European application No. 20892269.0.

Office Action issued on May 9, 2023 in corresponding Japanese Patent Application No. 2022-530769, 4 pp.

Seo, Bo-Bae et al., "Tuning physical properties and BMP-2 release rates of injectable hydrogel systems for an optimal bone regeneration effect", (2017), Biomaterials, vol. 122, pp. 91-104.

Zhang, Kaiwen et al., "Thermo-Responsive Hydrogels: From Recent Progress to Biomedical Applications", (2021), Gels, vol. 7, No. 3:77. https://doi.org/10.3390/gels7030077.

* cited by examiner

Example 4

Comparative Example 3

Example 11 in 37 °C Cell culture media

Example 13 in 37 °C Cell culture media

Comparative
Example 7    Example 11 in 37 °C PBS solution

Example 13

Example 13

Comparative
Example 8

Example 11 | Comparative Example 7

COMPOSITION OF THERMOSENSITIVE HYDROGELS HAVING ALTERED REVERSIBLE SOL-GEL TRANSITION PROPERTY, AND USE THEREOF

TECHNICAL FIELD

The present invention relates to a thermosensitive hydrogel composition, which while comprising an amino acid ester, polyethylene glycol, and a functional group for the introduction of a functional moiety at an end thereof at a predetermined ratio, comprises a polyphosphazene-based polymer having a controlled length and a content of polyethylene glycol contained therein, in which a reversible sol-gel transition character is altered; a medical polymer hydrogel comprising the polyphosphazene-based polymer; or an ink composition for 3D printing.

BACKGROUND ART

A thermosensitive polymer hydrogel exhibits a sol-gel phase transition that it is maintained in a liquid state (e.g., a sol phase) at low temperature while the sol is changed into a gel as the temperature increases. The sol-gel phase transition of a thermosensitive polymer hydrogel has advantages in that since the hydrogel is injected as a liquid, it can be evenly distributed over lesions regardless of the shape of the tissue to which the hydrogel is to be applied, and that since the hydrogel can be instantly formed into a three-dimensional gel by the body temperature, it can be effectively present in a form suitable for the application site, thus having a great potential as an injectable hydrogel for drug storage or a tissue adhesive material. However, considering the risk of loss of or morphological changes in a hydrogel due to low strength and temperature sensitivity, it is only used for limited medical applications.

The present inventors have confirmed through previous studies that phosphazene-based polymers prepared by substituting an amino acid ester and methoxypolyethylene glycol to a dichlorophosphazene linear polymer exist as a solution at a certain temperature or below, but, these phosphazene-based polymers have a property as a thermosensitive polymer which exhibits a sol-gel phase transition in a gel state of a three-dimensional structure when the temperature goes beyond a certain temperature (Korea Patent Nos. 10-0259367 and 10-0315630).

However, although the hydrogel containing a thermosensitive polymer as an active ingredient has an advantage in that it can combine and treat drugs to be administered for a long-term period or various materials that function for tissue regeneration, it is mainly used in conditions where a three-dimensional structure can be maintained in the human body after it is injected into the body due to its sol-gel phase transition property, which is sensitive to temperature changes. The hydrogel was sufficient to be used as a drug delivery system in a place where body temperature homeostasis is well maintained, but there are limited fields of application due to the property of reversible thermosensitivity.

SUMMARY

The present inventors have made extensive efforts to overcome the limitation of application fields caused by the reversible transition according to the temperature change after gel formation by changing the sol-gel transition property of thermosensitive phosphazene-based polymers. As a result, they have found that, by adjusting the proportion of the polyethylene glycol moiety substituted to the polyphosphazene backbone to an appropriate range according to the length of the polyethylene glycol moiety, the solution containing the polyethylene glycol moiety can remain in a liquid state from low temperature to room temperature and can be gelled near the body temperature of 37° C., whereas it is not reversibly transferred to a solution and maintains the strength and/or shape of the formed gel even when the temperature changes (e.g., a temperature drops back to room temperature, etc.), thereby completing the present invention.

A first aspect of the present invention provides thermosensitive hydrogel composition, in which a reversible sol-gel transition characteristic is altered, comprising a polyphosphazene-based polymer, comprising:
  a first moiety of an amino acid ester of Formula 2 below;
  a second moiety of polyethylene glycol of Formula 3 below; and
  a third moiety comprising at an end a functional group for the introduction of a functional moiety,
  on a phosphorous atom of a polyphosphazene backbone of Formula 1 below at a ratio of a:b:c, respectively,

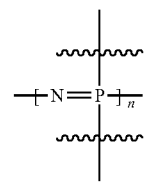

[Formula 1]

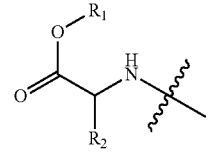

[Formula 2]

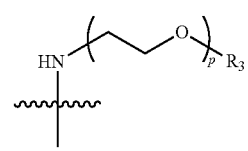

[Formula 3]

wherein, in Formulas 1 to 3 above,
$R_1$ is $C_{1-6}$ alkyl, ($C_{1-6}$ alkenyl), or $C_{6-10}$ aryl-$C_{1-6}$ alkyl,
$R_2$ is hydrogen, methyl, isopropyl, 1-methylpropyl, 2-methylpropyl, thiomethyl, methylthioethyl, benzyl, hydroxybenzyl, or 2-indolylmethyl,
$R_3$ is $C_{1-6}$ alkyl,
n is an integer of 3 to 100,000, and
p is an integer of 1 to 20,
wherein, based on all of the binding sites, (a+b) accounts for 80% to 99% and c accounts for 1% to 20%,
i) when p is 1 to 11, b is in a range of 25% to less than 40%,
ii) when p is 12 to 16, b is in a range of 10% to 20%, and
iii) when p is 16 to 20, b is in a range of 10% to 15%.

A second aspect of the present invention provides a composition for tissue regeneration comprising the phosphazene-based polymer.

A third aspect of the present invention provides a drug delivery system comprising the polyphosphazene-based polymer and a functional material.

A fourth aspect of the present invention provides an ink composition for 3D printing comprising the phosphazene-based polymer.

Hereinafter, the present invention will be described in detail.

Generally, a thermosensitive polymer is a polymer which exhibits a sudden change in solubility according to a temperature change. As the temperature is raised, the hydrogen bond between a polymer and a solvent is weakened to cause dehydration and the hydrophobic attraction between the polymers is enhanced, thereby resulting in a more hydrophobic structure. At the low critical solution temperature (LCST), a polymer-polymer interaction and a water-water interaction are more preferred than a hydrogen bond between a polymer and water, and thus, dehydration occurs rapidly in the polymer thereby resulting in a more hydrophobic structure.

In thermosensitive polymers, the low critical solution temperature (LCST) changes according to the balance between the hydrophobic groups and the hydrophilic groups, which are bound to the polymer backbone. Generally, when the content of the hydrophilic groups increases, the phase transition temperature increases, whereas when the content of the hydrophobic groups increases, the phase transition temperature decreases.

Among these thermosensitive polymers, a polyphosphazene backbone-based polymer is maintained in a solution state at room temperature due to its thermosensitivity, and when it is injected into the body, it is gelled by the body temperature to form a three-dimensional structure, and is gradually degraded in the body due to their biodegradability. Therefore, it is possible to form an implant by injecting the polymer in the form of an injection to a desired site, or injecting it along with a drug after mixing as needed such that the drug can be slowly released according to the degradation of the structure, and thus, the polyphosphazene backbone-based polymer can be used as a drug delivery system.

However, due to transition reversibility of the polymer, that the polymer returns back to a solution state according to temperature change once it leaves the body environment, not only its field of application may be limited to injections into the body, but also its effect as an implant may not be exhibited because the injected hydrogel loses its shape due to the loss of the body temperature by the external environment when it is applied under a thin skin membrane which is significantly affected by the external temperature (e.g., face, hands, and feet), open wound areas, gums or implant areas, etc., or simultaneously therewith, the drug may be released excessively to cause side effects in a case where the drug is contained in the polymer, thereby limiting its use.

The present invention is designed to overcome the limitation of the use of thermosensitive phosphazene-based polymer due to its reversible sol-gel transition property. The present invention is based on the discovery that when the essential constituent moieties constituting the polymer have a predetermined ratio, the sol-gel transition of the polymer solution reversibly occurs due to temperature change below a certain temperature, whereas after exposure to a certain temperature or above, the sudden reversible transition property of the polymer is lost and its gel shape is maintained for a long period of time. Specifically, the above-described property appears only when substituents are introduced to the polyphosphazene backbone at a certain ratio, and it is possible for the polymer to have such a change in property by the proportion of the substituents introduced during the initial polymer synthesis regardless of the polymer concentration and/or composition in the aqueous polymer solution.

As such, the present invention provides a thermosensitive hydrogel composition, in which a reversible sol-gel transition characteristic is altered, comprising a polyphosphazene-based polymer, comprising:

a first moiety of an amino acid ester of Formula 2 below;
a second moiety of polyethylene glycol of Formula 3 below; and
a third moiety comprising at an end a functional group for the introduction of a functional moiety,
on a phosphorous atom of a polyphosphazene backbone of Formula 1 below at a ratio of a:b:c, respectively,

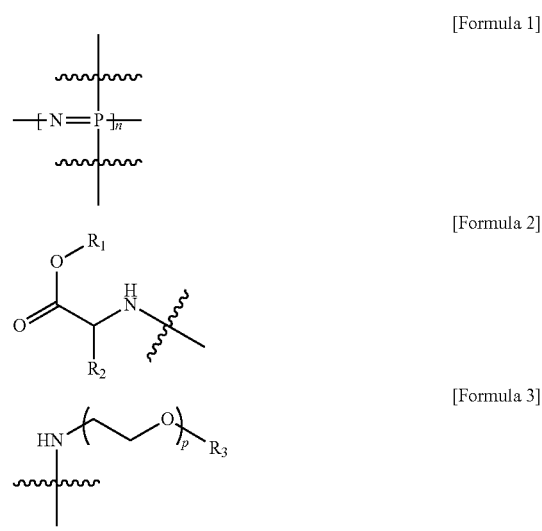

wherein, in Formulas 1 to 3 above,
$R_1$ is $C_{1-6}$ alkyl, ($C_{1-6}$ alkenyl), or $C_{6-10}$ aryl-$C_{1-6}$ alkyl,
$R_2$ is hydrogen, methyl, isopropyl, 1-methylpropyl, 2-methylpropyl, thiomethyl, methylthioethyl, benzyl, hydroxybenzyl, or 2-indolylmethyl,
$R_3$ is $C_{1-6}$ alkyl,
n is an integer of 3 to 100,000, and
p is an integer of 1 to 20,
wherein, based on all of the binding sites, (a+b) accounts for 80% to 99% and c accounts for 1% to 20%,
i) when p is 1 to 11, b is in a range of 25% to less than 40%,
ii) when p is 12 to 16, b is in a range of 10% to 20%, and
iii) when p is 16 to 20, b is in a range of 10% to 15%.

With regard to the hydrogel composition of the present invention, in the third moiety which is contained in the phosphazene-based polymer, the functional group for the introduction of a functional moiety may be selected from the group consisting of an amino acid, a peptide, a depsipeptide, a depsipeptide ester, an amide group, an amino group, a sulfate group, a thiol group, a vinyl group, an aldehyde group, an acrylate group, a methacrylate group, a hydroxyl group, and a carboxyl group.

For example, in the above Formulas, $R_1$ may be methyl, ethyl, propyl, butyl, benzyl, or 2-propenyl.

For example, in the above Formulas, $R_3$ may be methyl, but is not limited thereto.

The thermosensitive hydrogel composition may further comprise a fourth moiety comprising at least one functional moiety linked directly or by a linker to all or part of the functional group of the fourth moiety, wherein the functional moiety is selected from the group consisting of a material capable of regulating a degradation rate of the polymer, a substituent comprising an ionic group capable of regulating a degradation rate, a substituent capable of cross-linking, an additional compound capable of inducing tissue adhesion, a physiologically active material, and a composite material formed by linear connection of two or more materials thereof.

In particular, the fourth moiety may include at least one selected from the group consisting of folic acid, hyaluronic acid, cyclodextrin, an imidazole-based compound, an anticancer agent, histidine, lysine, arginine, cysteine, thiolarylamine, spermine, spermidine, polyethylenimine, polyhistidine, polylysine, polyarginine, protamine, heparin, chitosan, and a peptide consisting of 1 to 20 amino acids.

The thermosensitive hydrogel composition of the present invention, in which a reversible sol-gel transition property is altered, may be a solution in which the polyphosphazene-based polymer is dissolved in a solvent at a concentration of 1 wt % to 50 wt %.

In particular, as the solvent, at least one kind selected from the group consisting of water, a buffer solution, an acidic solution, a basic solution, a salt solution, normal saline, water for injection, a cell culture medium, and dextrose saline may be used, but the solvent is not limited thereto.

For example, the thermosensitive hydrogel composition of the present invention, in which a reversible sol-gel transition property is altered, may show a sol-gel behavior at a temperature of 5° C. to 70° C. and may form a hydrogel at a predetermined particular temperature.

Furthermore, the thermosensitive hydrogel composition of the present invention, in which a reversible sol-gel transition property is altered, may be designed such that while it is gelled when applied in vivo or in an ex vivo environment, it is able to maintain its gel state regardless of changes in temperature by losing its temperature sensitivity at a predetermined particular temperature.

Additionally, the present invention provides a thermosensitive hydrogel composition for tissue regeneration comprising a polyphosphazene-based polymer, wherein the polyphosphazene-based polymer comprises:
 a first moiety of an amino acid ester of Formula 2 below;
 a second moiety of polyethylene glycol of Formula 3 below; and
 a third moiety comprising at an end a functional group for the introduction of a functional moiety,
 on a phosphorous atom of a polyphosphazene backbone of Formula 1 below at a ratio of a:b:c, respectively,

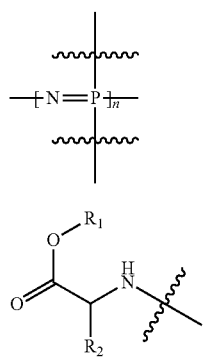

[Formula 1]

[Formula 2]

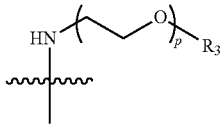

[Formula 3]

wherein, in Formulas 1 to 3 above, $R_1$ is $C_{1-6}$ alkyl, ($C_{1-6}$ alkenyl), or $C_{6-10}$ aryl-$C_{1-6}$ alkyl, $R_2$ is hydrogen, methyl, isopropyl, 1-methylpropyl, 2-methylpropyl, thiomethyl, methylthioethyl, benzyl, hydroxybenzyl, or 2-indolylmethyl, $R_3$ is $C_{1-6}$ alkyl, n is an integer of 3 to 100,000, and p is an integer of 1 to 20, wherein, based on all of the binding sites, (a+b) accounts for 80% to 99% and c accounts for 1% to 20%, i) when p is 1 to 11, b is in a range of 25% to less than 40%, ii) when p is 12 to 16, b is in a range of 10% to 20%, and iii) when p is 16 to 20, b is in a range of 10% to 15%.

As described above, the thermosensitive hydrogel composition of the present invention for tissue regeneration may be designed such that while the composition is gelled when applied in vivo or in an ex vivo environment, it is able to maintain its gel state regardless of changes in temperature by losing its temperature sensitivity at a predetermined particular temperature.

The maintenance of the gel state can provide a space for cells to adhere and survive, such that the composition, after being gelled when applied in vivo or in an ex vivo environment, stably maintains its shape and volume against changes in temperature inside and outside of the body, thereby allowing the cells to be introduced and replaced with autologous tissue.

Additionally, the present invention provides a drug delivery system comprising a polyphosphazene-based polymer and a functional material, wherein the polyphosphazene-based polymer comprises:
 a first moiety of an amino acid ester of Formula 2 below;
 a second moiety of polyethylene glycol of Formula 3 below; and
 a third moiety comprising at an end a functional group for the introduction of a functional moiety,
 on a phosphorous atom of a polyphosphazene backbone of Formula 1 at a ratio of a:b:c, respectively,

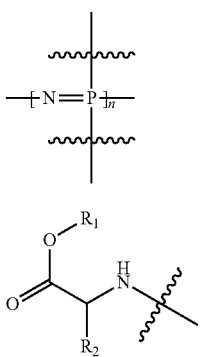

[Formula 1]

[Formula 2]

[Formula 3]

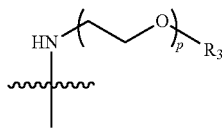

wherein, in Formulas 1 to 3 above, $R_1$ is $C_{1-6}$ alkyl, ($C_{1-6}$ alkenyl), or $C_{6-10}$ aryl-$C_{1-6}$ alkyl, $R_2$ is hydrogen, methyl, isopropyl, 1-methylpropyl, 2-methylpropyl, thiomethyl, methylthioethyl, benzyl, hydroxybenzyl, or 2-indolylmethyl, $R_3$ is $C_{1-6}$ alkyl, n is an integer of 3 to 100,000, and p is an integer of 1 to 20, wherein, based on all of the binding sites, (a+b) accounts for 80% to 99% and c accounts for 1% to 20%, i) when p is 1 to 11, b is in a range of 25% to less than 40%,
ii) when p is 12 to 16, b is in a range of 10% to 20%, and
iii) when p is 16 to 20, b is in a range of 10% to 15%.

For example, the drug delivery system of the present invention may include drugs, cells, nanoparticles, microparticles, physiologically active materials, or a combination thereof, as a functional material.

The functional material may be cells (e.g., preosteoblasts, chondrocytes, umbilical vein endothelial cells (UVEC), osteoblasts, adult stem cells, Schwann cells, oligodendrocytes, hepatocytes, mural cells (treatment in combination with UVEC), myoblasts, insulin-secreting cells, endothelial cells, smooth muscle cells, fibroblasts, jcells, endodermal cells, hepatic stem cells, juxtaglomerular cells, skeletal muscle cells, keratinocytes, melanocytes, Langerhans cells, Merkel cells, dermal fibroblasts, preadipocytes, etc.); genes (e.g., small interference RNAs (siRNAs), plasmid DNAs, antisense oligodeoxynucleotides (AS-ODN), etc.); proteins, peptides or polypeptides (e.g., exendin-4, erythropoietin (EPO), interferon-alpha, interferon-beta, interferon-gamma, growth hormone, growth hormone releasing factors, nerve growth factor, granulocyte-colony stimulating factors (G-CSFs), granulocyte macrophage-colony stimulating factors (GM-CSFs), macrophage-colony stimulating factors (M-CSFs), blood clotting factors, insulin, oxytocin, vasopressin, adrenocorticotropic hormone, fibroblast growth factors, epidermal growth factors, platelet-derived growth factors, insulin-like growth factors, vascular endothelial growth factors, transforming growth factors, brain nerve growth factors, neurotrophin-3 (NT-3), neurotrophin-4/5, prolactin, luliberin, luteinizing hormone releasing hormone (LHRH), LHRH agonists, LHRH antagonists, somatostatin, glucagon, interleukin-2 (IL-2), interleukin-11 (IL-11), gastrin, tetragastrin, pentagastrin, urogastrone, secretin, calcitonin, enkephalin, endorphin, angiotensin, thyrotropin releasing hormone, tumor necrosis factors, tumor necrosis factor-related apoptosis-inducing ligands (TRAILs), heparinase, bone morphogenic protein, human atrial natriuretic peptides (hANPs), glucagon-like peptides, renin, bradykinin, bacitracin, polymyxin, colistin, tyrocidine, gramicidin, cyclosporin, neurotensin, tachykinin, neuropeptide Y, peptide YY, vasoactive intestinal polypeptides, pituitary adenylate cyclase-activating polypeptides, and antibodies specific thereto, enzymes and/or cytokines, etc.), peptides or polypeptides; vaccines (e.g., hepatitis vaccines, etc.); hormones (e.g., testosterone, estradiol, progesterone, prostaglandin, etc.); anticancer drugs (e.g., paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxyprogesterone acetate, epirubicin, letrozole, pirarubicin, topotecan, altretamine, toremifene citrate, BCNU, taxotere, actinomycin D, anastrozole, belotecan, imatinib, floxuridine, gemcitabine, hydroxyurea, zoledronate, flutamide, valrubicin, streptozocin, and polyethylene glycol-conjugated derivatives thereof, etc.); angiogenesis inhibitors (e.g., clodronate, 6-deoxy-6-demethyl-4-dedimethylaminotetracycline (COL-3), doxycycline, marimastat, 2-methoxyestradiol, squalamine, thalidomide, TNP-470, combretastatin A4, soy isoflavone, enzastaurin, revimid, celecoxib, vandetanib, halofuginone hydrobromide, interferon-alpha, bevacizumab, shark cartilage extract, interleukin-12, vascular endothelial growth factor-trap (VEFG-trap), cetuximab, rebimastat, matrix metalloproteinase (MMP) inhibitors, protein kinase C beta inhibitors, endostatin, vatalanib, sunitinib malate, cilengitide, humanized monoclonal antibodies, volociximab, integrin alpha-5-beta-1 antagonists, etc.); or a combination thereof.

Specifically, the drug delivery system of the present invention may further include at least one kind of a cationic polymer selected from the group consisting of polyarginine, polylysine, polyethylene glycol, polyethylenimine, chitosan, and protamine having a weight average molecular weight of 200 to 750,000; at least one kind of an anionic polymer selected from the group consisting of polyvinyl acetate, hyaluronic acid, chondroitin sulfate, heparin, and alginate having a weight average molecular weight of 200 to 750,000; and at least one kind of an additive, which is selected from the group consisting of amino acids, peptides, proteins, fatty acids, phospholipids, vitamins, polyethylene glycol ester, steroids, amine compounds, acrylic copolymers, organic solvents, preservatives, sugars, polyols, sugar-containing polyols, sugar-containing amino acids, surfactants, sugar-containing ions, silicates, metal salts, and ammonium salts, in an amount of $1\times10^{-6}$ wt % to 30 wt %.

Furthermore, the present invention provides an ink composition for 3D printing comprising a polyphosphazene-based polymer, wherein the polyphosphazene-based polymer comprises:

a first moiety of an amino acid ester of Formula 2 below;

a second moiety of polyethylene glycol of Formula 3 below; and a third moiety comprising at an end a functional group for the introduction of a functional moiety, on a phosphorous atom of a polyphosphazene backbone of Formula 1 below at a ratio of a:b:c, respectively,

[Formula 1]

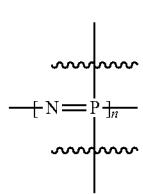

-continued

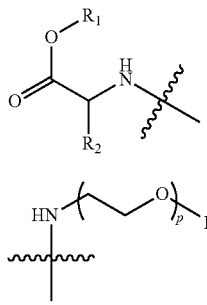
[Formula 2]

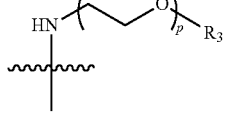
[Formula 3]

wherein, in Formulas 1 to 3 above,
$R_1$ is $C_{1-6}$ alkyl, ($C_{1-6}$ alkenyl), or $C_{6-10}$ aryl-$C_{1-6}$ alkyl,
$R_2$ is hydrogen, methyl, isopropyl, 1-methylpropyl, 2-methylpropyl, thiomethyl, methylthioethyl, benzyl, hydroxybenzyl, or 2-indolylmethyl,
$R_3$ is $C_{1-6}$ alkyl,
n is an integer of 3 to 100,000, and
p is an integer of 1 to 20,
wherein, based on all of the binding sites, (a+b) accounts for 80% to 99% and c accounts for 1% to 20%,
i) when p is 1 to 11, b is in a range of 25% to less than 40%,
ii) when p is 12 to 16, b is in a range of 10% to 20%, and
iii) when p is 16 to 20, b is in a range of 10% to 15%.

For example, the ink composition of the present invention for 3D printing is characterized in that it maintains a liquid state at room temperature, and it is gelled after printing at a predetermined particular temperature or higher where it loses its thermosensitivity such that the printed product maintains a gel state regardless of changes in temperature.

For example, the ink composition of the present invention for 3D printing may further include at least one kind of a cell so as to prepare a biomimetic material for transplantation or a biomimetic material for drug tests. Specifically, since the ink composition of the present invention for 3D printing exhibits a property as a thermosensitive hydrogel, in which a reversible sol-gel transition is altered as described above, the ink composition can be cultured into a desired 3D form in such a manner that the cells to be used in the polymer solution are mixed at temperature where the solution state can be maintained, the mixture is injected into a 3D printing cartridge to be printed into a desired form, the resultant is solidified via gelling by increasing the temperature, and the solidified resultant is cultured in a culture medium. In a specific embodiment of the present invention, the survival rate of cells was measured by culturing the 3D-printed structure, which was obtained by adding cells to the ink composition of the present invention for 3D printing as described above, in a cell culture medium, and it was confirmed that the cells maintained a survival rate close to 100% without side effects such as toxicity even for a long-term culture of 21 days (FIG. 4).

Advantageous Effects

The thermosensitive hydrogel composition of the present invention, which comprises a phosphazene-based polymer, can maintain its shape without being rapidly changed to a solution phase even when the temperature changes again after gelation at a predetermined temperature, by changing the sol-gel transition property according to temperature of the hydrogel formed therefrom, by controlling the moieties bound thereto, and in particular, by controlling the content of polyethylene glycol. Therefore, the thermosensitive hydrogel composition of the present invention can be used as an in vivo implant by presetting the composition to be gelled at the body temperature or may be utilized for tissue recovery or a tissue regeneration structure and/or a drug delivery system by further adding a drug, a physiologically active material, etc. thereto.

DETAILED DESCRIPTION OF THE INVENTION

Figure 1:
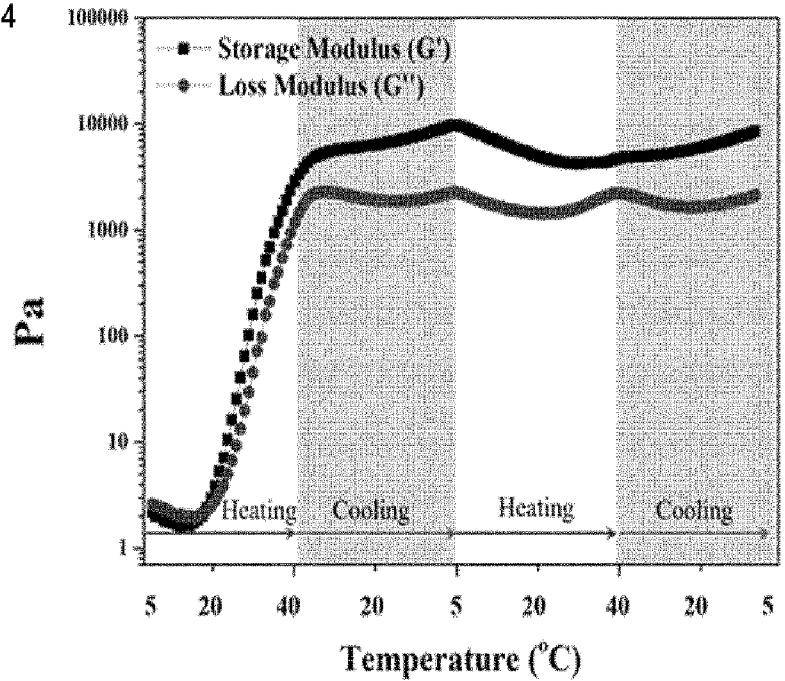
FIG. 1 shows the graphs illustrating the changes in storage modulus (G') and loss modulus (G") according to the repeated temperature changes in the phosphazene-based polymer solutions according to the Examples and Comparative Examples of the present invention.
Figure 1:
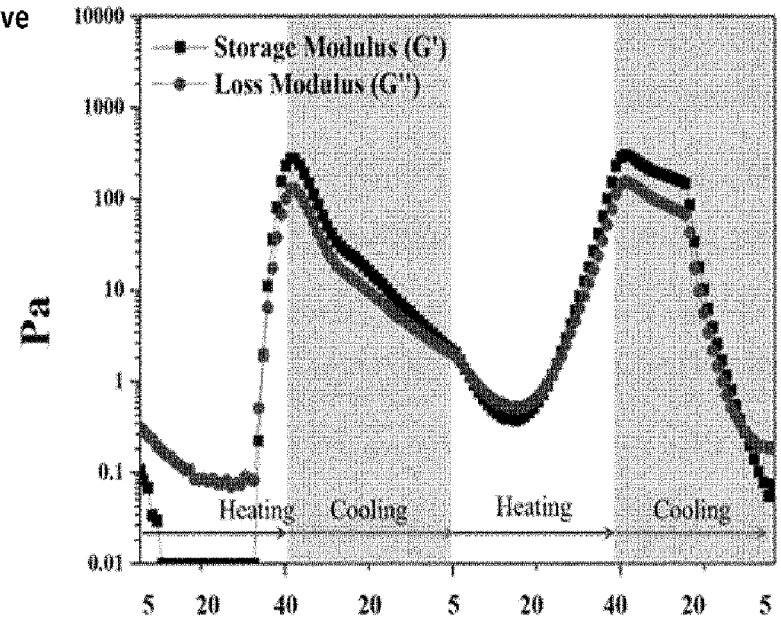

Hereinafter, the present invention will be described in more detail with reference to the following Examples. However, these Examples are for illustrative purposes only and the scope of the invention is not limited by these Examples.

<Identification of Compounds>

In the following Examples, for the identification of synthesized polymers, carbon, hydrogen, and nitrogen elements were analyzed using the C, H, and N analyzer (Perkin-Elmer Inc.) in the Advanced Analysis Center of the Korea Institute of Science and Technology (KIST). In addition, hydrogen and phosphorus nuclear magnetic resonance spectra were measured with a Varian Gemini-300, and the weight average molecular weight (Mw) was measured by a Waters 1515 pump and 2410 differential refractometer gel permeation chromatography.

Example 1: Preparation of poly[(isoleucineethylester)$_{1.19}$(aminomethoxypolyethylene Glycol 550)$_{0.79}$(ethyl-2-(O-glycyl)lactate)$_{0.02}$phosphazene]$_n$ Dry isoleucine ethyl ester hydrochloride (IleOEt·HCl, 20.09 g) was dissolved in anhydrous tetrahydrofuran (THF) containing triethylamine. A solution, in which polydichlorophosphazene (10 g) was dissolved in anhydrous THF, was added dropwise to the above solution in a dry ice-acetone bath and the temperature was gradually increased to 40° C. to 50° C. and reacted for 24 hours. After the reactants were cooled to room temperature, dry ethyl-2-(O-glycyl)lactate ammonium oxalate (0.52 g) was added to the reactants by adding anhydrous acetonitrile to which triethylamine was added and reacted at 40° C. to 50° C. for 24 hours by slowly increasing the temperature.

After the reactants were cooled to room temperature, dried polyethylene glycol (37.49 g, MW: 550) was dissolved in anhydrous THF, and the solution to which triethylamine was added was added to the reactants, and reacted for 24 hours by increasing the temperature to 40° C. to 50° C. The resulting solution in which the reaction was completed was filtered to remove the formed triethylamine hydrochloride, and the reaction filtrate was concentrated under reduced pressure until only a small amount of the solvent remained. The concentrate was dissolved in anhydrous THF and an excess amount of hexane was added to induce precipitation. After repeating the above process 2 or 3 times, the precipitate was dissolved again in a small amount of methanol, put into an MWCO 12000 membrane (Spectrum Laboratories, Inc.), dialyzed with methanol at room temperature for 4 days, dialyzed with distilled water for 4 days, and dried at low temperature to obtain a polyphosphazene polymer, [NP(IleOEt)$_{1.19}$(AMPEG550)$_{0.79}$(GlyLacOEt)$_{0.02}$]$_n$, which contains isoleucineethylester, aminomethoxypolyethylene glycol, and ethyl-2-(O-glycyl)lactate.

$^1$H NMR Spectrum (CDCl$_3$, ppm):
δ 0.8-1.1 (b, —NHCH(CH(C$\underline{H_3}$)CH$_2$CH$_3$)COOCH$_2$CH$_3$),
δ 1.1-1.4 (b, —NHCH(CH(CH$_3$)C$\underline{H_2}$CH$_3$)COOCH$_2$C$\underline{H_3}$),
δ 1.3-1.5 (b, —NHCH$_2$COOCH(CH$_3$)COOCH$_2$C$\underline{H_3}$),
δ 1.4-1.8 (b, —NHC$\underline{H}$(CH(CH$_3$)CH$_2$CH$_3$)COOCH$_2$CH$_3$),
δ 1.6-1.7 (b, —NHCH$_2$COOCH(C$\underline{H_3}$)COOCH$_2$CH$_3$),
δ 2.67-3.2 (b, —NH(CH$_2$CH$_2$O)$_{11}$C$\underline{H_3}$),
δ 3.4 (s, —NH(CH$_2$CH$_2$O)$_{11}$C$\underline{H_3}$),
δ 3.4-3.9 (b, —NH(C$\underline{H_2}$C$\underline{H_2}$O)$_{11}$CH$_3$, —NHC$\underline{H}$(CH(CH$_3$)CH$_2$CH$_3$)COOCH$_2$CH$_3$),
δ 3.9-4.3 (b, —NHCH(CH(CH$_3$)CH$_2$CH$_3$)COOC$\underline{H_2}$CH$_3$),
δ 4.0-4.4 (b, —NHC$\underline{H_2}$COOCH(CH$_3$)COOC$\underline{H_2}$CH$_3$),
δ 5.2-5.4 (b, —NHCH$_2$COOC$\underline{H}$(CH$_3$)COOC$\underline{H_2}$CH$_3$),
Average molecular weight ($\overline{M_w}$): 23,000

Example 2: Preparation of poly[(isoleucineethylester)$_{1.56}$(aminomethoxypolyethylene Glycol 750)$_{0.39}$(ethyl-2-(O-glycyl)lactate)$_{0.05}$phosphazene]$_n$ Isoleucine ethyl ester hydrochloride (26.34 g), polydichlorophosphazene (10 g), ethyl-2-(O-glycyl)lactate ammonium oxalate (52 g), and polyethylene glycol (25.23 g; MW: 750) were reacted in the same manner as in Example 1 to obtain the final product, [NP(IleOEt)$_{1.56}$(AMPEG750)$_{0.39}$(GlyLacOEt)$_{0.05}$]$_n$.

$^1$H NMR Spectrum (CDCl$_3$, ppm):
δ 0.8-1.1 (b, —NHCH(CH(C$\underline{H_3}$)CH$_2$CH$_3$)COOCH$_2$CH$_3$),
δ 1.1-1.4 (b, —NHCH(CH(CH$_3$)C$\underline{H_2}$CH$_3$)COOCH$_2$C$\underline{H_3}$),
δ 1.3-1.5 (b, —NHCH$_2$COOCH(CH$_3$)COOCH$_2$C$\underline{H_3}$),
δ 1.4-1.8 (b, —NHC$\underline{H}$(CH(CH$_3$)CH$_2$CH$_3$)COOCH$_2$CH$_3$),
δ 1.6-1.7 (b, —NHCH$_2$COOCH(C$\underline{H_3}$)COOCH$_2$CH$_3$),
δ 2.67-3.2 (b, —NH(CH$_2$CH$_2$O)$_{11}$C$\underline{H_3}$),
δ 3.4 (s, —NH(CH$_2$CH$_2$O)$_{16}$C$\underline{H_3}$),
δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.9-4.3 (b, —NHCH(CH(CH$_3$)CH$_2$CH$_3$)COOC$\underline{H_2}$CH$_3$),
δ 4.0-4.4 (b, —NHC$\underline{H_2}$COOCH(CH$_3$)COOC$\underline{H_2}$CH$_3$),
δ 5.2-5.4 (b, —NHCH$_2$COOC$\underline{H}$(CH$_3$)COOC$\underline{H_2}$CH$_3$),
Average molecular weight ($\overline{M_w}$): 19,000

Example 3: Preparation of poly[(isoleucineethylester)$_{1.77}$(aminomethoxypolyethylene Glycol 1000)$_{0.21}$(ethyl-2-(O-glycyl)lactate)$_{0.02}$phosphazene]$_n$ Isoleucine ethyl ester hydrochloride (29.88 g), polydichlorophosphazene (10 g), ethyl-2-(O-glycyl)lactate ammonium oxalate (52 g), and polyethylene glycol (18.12 g; MW: 1,000) were reacted in the same manner as in Example 1 to obtain the final product, [NP(IleOEt)$_{1.77}$(AMPEG1000)$_{021}$(GlyLacOEt)$_{0.02}$]$_n$.

$^1$H NMR Spectrum (CDCl$_3$, ppm):
δ 0.8-1.1 (b, —NHCH(CH(C$\underline{H_3}$)CH$_2$CH$_3$)COOCH$_2$CH$_3$),
δ 1.1-1.4 (b, —NHCH(CH(CH$_3$)C$\underline{H_2}$CH$_3$)COOCH$_2$C$\underline{H_3}$),
δ 1.3-1.5 (b, —NHCH$_2$COOCH(CH$_3$)COOCH$_2$C$\underline{H_3}$),
δ 1.4-1.8 (b, —NHC$\underline{H}$(CH(CH$_3$)CH$_2$CH$_3$)COOCH$_2$CH$_3$),
δ 1.6-1.7 (b, —NHCH$_2$COOCH(C$\underline{H_3}$)COOCH$_2$CH$_3$),
δ 2.67-3.2 (b, —NH(CH$_2$CH$_2$O)$_{20}$C$\underline{H_3}$),
δ 3.4 (s, —NH(CH$_2$CH$_2$O)$_{20}$C$\underline{H_3}$), δ 3.4-3.9 (b, —NH(C$\underline{H_2}$C$\underline{H_2}$O)$_{20}$CH$_3$, —NHC$\underline{H}$(CH(CH$_3$)CH$_2$CH$_3$)COOC$\underline{H_2}$C$\underline{H_3}$),
δ 3.9-4.3 (b, —NHCH(CH(CH$_3$)CH$_2$CH$_3$)COOC$\underline{H_2}$CH$_3$),
δ 4.0-4.4 (b, —NHC$\underline{H_2}$COOCH(CH$_3$)COOC$\underline{H_2}$CH$_3$),
δ 5.2-5.4 (b, —NHC$\underline{H_2}$COOC$\underline{H}$(CH$_3$)COOC$\underline{H_2}$CH$_3$),
Average molecular weight (M$_w$): 48,000

Example 4: Preparation of poly[(isoleucineethylester)$_{1.29}$(aminomethoxypolyethylene Glycol 550)$_{0.50}$(aminoethanol)$_{0.21}$phosphazene]$_n$ Isoleucine ethyl ester hydrochloride (21.61 g), polydichlorophosphazene (10 g), aminoethanol (1.21 g), and polyethylene glycol (23.25 g; MW: 550) were reacted in the same manner as in Example 1, except that THF was used instead of anhydrous acetonitrile when aminoethanol was added, to obtain the final product, [NP(IleOEt)$_{1.29}$(AMPEG550)$_{0.50}$(Aminoethanol)$_{0.21}$]$_n$.

$^1$H NMR Spectrum (CDCl$_3$, ppm):
δ 0.8-1.1 (b, —NHCH(CH(C$\underline{H_3}$)CH$_2$CH$_3$)COOCH$_2$CH$_3$),
δ 1.1-1.4 (b, —NHCH(CH(CH$_3$)C$\underline{H_2}$CH$_3$)COOCH$_2$CH$_3$),
δ 1.4-1.8 (b, —NHC$\underline{H}$(C$\underline{H}$(CH$_3$)CH$_2$CH$_3$)COOCH$_2$CH$_3$),
δ 2.67-3.2 (b, —NHCH$_2$C$\underline{H_2}$OH, —NH(CH$_2$CH$_2$O)$_{11}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{11}$C$\underline{H_3}$),
δ 3.4-3.9 (b, —NH(C$\underline{H_2}$C$\underline{H_2}$O)$_{11}$CH$_3$, —NHC$\underline{H}$(CH(CH$_3$)CH$_2$CH$_3$)COOC$\underline{H_2}$C$\underline{H_3}$),
δ 3.9-4.3 (b, —NHCH(CH(CH$_3$)CH$_2$CH$_3$)COOC$\underline{H_2}$CH$_3$),
Average molecular weight (M$_w$): 8,800

Example 5: Preparation of poly[(isoleucineethylester)$_{1.45}$(aminomethoxypolyethylene Glycol 750)$_{0.32}$(aminoethanol)$_{0.23}$phosphazene]$_n$ Isoleucine ethyl ester hydrochloride (24.48 g), polydichlorophosphazene (10 g), aminoethanol (1.21 g), and polyethylene glycol (20.70 g; MW: 750) were reacted in the same manner as in Example 1, except that THF was used instead of anhydrous acetonitrile when aminoethanol was added, to obtain the final product, [NP(IleOEt)$_{1.45}$(AMPEG750)$_{0.32}$(Aminoethanol)$_{0.23}$]$_n$.

$^1$H NMR Spectrum (CDCl$_3$, ppm):
δ 0.8-1.1 (b, —NHCH(CH(C$\underline{H_3}$)CH$_2$CH$_3$)COOCH$_2$CH$_3$),
δ 1.1-1.4 (b, —NHCH(CH(CH$_3$)C$\underline{H_2}$CH$_3$)COOCH$_2$CH$_3$),
δ 1.4-1.8 (b, —NHC$\underline{H}$(C$\underline{H}$(CH$_3$)CH$_2$CH$_3$)COOCH$_2$CH$_3$),
δ 2.67-3.2 (b, —NHCH$_2$C$\underline{H_2}$OH, —NH(CH$_2$CH$_2$O)$_{16}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{16}$C$\underline{H_3}$),
δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOC$\underline{H_2}$C$\underline{H_3}$),
δ 3.9-4.3 (b, —NHCH(CH(CH$_3$)CH$_2$CH$_3$)COOC$\underline{H_2}$CH$_3$),
Average molecular weight (M$_w$): 7,900

Example 6: Preparation of poly[(isoleucineethylester)$_{1.70}$(aminomethoxypolyethylene Glycol 1000)$_{0.20}$(aminoethanol)$_{0.10}$phosphazene]$_n$ Isoleucine ethyl ester hydrochloride (28.70 g), polydichlorophosphazene (10 g), aminoethanol (0.52 g), and polyethylene glycol (17.25 g; MW: 1,000) were reacted in the same manner as in Example 1, except that THF was used instead of anhydrous acetonitrile when aminoethanol was added, to obtain the final product, [NP(IleOEt)$_{1.70}$(AMPEG1000)$_{0.20}$(Aminoethanol)$_{0.10}$]$_n$.

$^1$H NMR Spectrum (CDCl$_3$, ppm):
δ 0.8-1.1 (b, —NHCH(CH(C$\underline{H_3}$)CH$_2$CH$_3$)COOCH$_2$CH$_3$),
δ 1.1-1.4 (b, —NHCH(CH(CH$_3$)C$\underline{H_2}$CH$_3$)COOCH$_2$C$\underline{H_3}$),
δ 1.4-1.8 (b, —NHC$\underline{H}$(C$\underline{H}$(CH$_3$)CH$_2$CH$_3$)COOCH$_2$CH$_3$),
δ 2.67-3.2 (b, —NHCH$_2$C$\underline{H_2}$OH, —NH(CH$_2$CH$_2$O)$_{20}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{20}$C$\underline{H_3}$),
δ 3.4-3.9 (b, —NH(C$\underline{H_2}$C$\underline{H_2}$O)$_{20}$CH$_3$, —NHC$\underline{H}$(CH(CH$_3$)CH$_2$CH$_3$)COOC$\underline{H_2}$C$\underline{H_3}$),
δ 3.9-4.3 (b, —NHCH(CH(CH$_3$)CH$_2$CH$_3$)COOC$\underline{H_2}$CH$_3$),
Average molecular weight (M$_w$): 14,000

Example 7: Preparation of poly[(isoleucineethylester)$_{1.21}$(aminomethoxypolyethylene Glycol 550)$_{0.61}$(aminoethylsuccinate)$_{0.18}$phosphazene]$_n$ Isoleucine ethyl ester hydrochloride (20.43 g), polydichlorophosphazene (10 g), aminoethanol (0.94 g), polyethylene glycol (28.94 g; MW: 550), anhydrous succinate (4.00 g), and dimethylaminopyridine (4.00 g) were reacted in the same manner as in Example 4 to obtain the final product, [NP(IleOEt)$_{1.21}$(AMPEG550)$_{0.61}$(Aminoethylsuccinate)$_{0.18}$]$_n$.

$^1$H NMR Spectrum (CDCl$_3$, ppm):
δ 0.8-1.1 (b, —NHCH(CH(C$\underline{H_3}$)CH$_2$CH$_3$)COOCH$_2$CH$_3$),
δ 1.1-1.4 (b, —NHCH(CH(CH$_3$)C$\underline{H_2}$CH$_3$)COOCH$_2$CH$_3$),
δ 1.4-1.8 (b, —NHC$\underline{H}$(C$\underline{H}$(CH$_3$)CH$_2$CH$_3$)COOCH$_2$CH$_3$),
δ 2.5-2.7 (b, —NHCH$_2$CH$_2$OCOC$\underline{H_2}$CH$_2$COOH),
δ 2.67-3.2 (b, —NHCH$_2$C$\underline{H_2}$OH, —NH(CH$_2$CH$_2$O)$_{11}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{11}$C$\underline{H_3}$),
δ 3.4-3.9 (b, —NH(C$\underline{H_2}$C$\underline{H_2}$O)$_{11}$CH$_3$, —NHC$\underline{H}$(CH(CH$_3$)CH$_2$CH$_3$)COOC$\underline{H_2}$C$\underline{H_3}$),
δ 3.9-4.3 (b, —NHCH(CH(CH$_3$)CH$_2$CH$_3$)COOC$\underline{H_2}$CH$_3$, —NHC$\underline{H_2}$OCOCH$_2$CH$_2$COOH),
Average molecular weight (M$_w$): 8,400

Example 8: Preparation of poly[(isoleucineethylester)$_{1.48}$(aminomethoxypolyethylene Glycol 750)$_{0.33}$(aminoethylsuccinate)$_{0.19}$phosphazene]$_n$ Isoleucine ethyl ester hydrochloride (24.99 g), polydichlorophosphazene (10 g), aminoethanol (1.00 g), polyethylene glycol (21.35 g; MW: 750), anhydrous succinate (4.00 g), and dimethylaminopyridine (4.00 g) were reacted in the same manner as in Example 7 to obtain the final product, [NP(IleOEt)$_{1.48}$(AMPEG750)$_{0.33}$(Aminoethylsuccinate)$_{0.19}$]$_n$.

$^1$H NMR Spectrum (CDCl$_3$, ppm):
δ 0.8-1.1 (b, —NHCH(CH(C$\underline{H_3}$)CH$_2$CH$_3$)COOCH$_2$CH$_3$),
δ 1.1-1.4 (b, —NHCH(CH(CH$_3$)C$\underline{H_2}$CH$_3$)COOCH$_2$C$\underline{H_3}$), δ 1.4-1.8 (b, —NHC$\underline{H}$(C$\underline{H}$(CH$_3$)CH$_2$CH$_3$)COOCH$_2$CH$_3$),
δ 2.5-2.7 (b, —NHCH$_2$CH$_2$OCOC$\underline{H_2}$CH$_2$COOH),
δ 2.67-3.2 (b, —NHCH$_2$C$\underline{H_2}$OH, —NH(CH$_2$CH$_2$O)$_{16}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{16}$C$\underline{H_3}$),
δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOC$\underline{H_2}$CH$_3$),
δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$COOH),
Average molecular weight (M$_w$): 6,700

Example 9: Preparation of poly[(isoleucineethylester)$_{1.70}$(aminomethoxypolyethylene Glycol 1000)$_{0.20}$(aminoethylsuccinate)$_{0.10}$phosphazene]$_n$ Isoleucine ethyl ester hydrochloride (28.70 g), polydichlorophosphazene (10 g), aminoethanol (0.52 g), polyethylene glycol (17.25 g; MW: 1,000), anhydrous succinate (4.00 g), and dimethylaminopyridine (4.00 g) were reacted in the same manner as in Example 7 to obtain the final product, [NP(IleOEt)$_{1.70}$(AMPEG1000)$_{0.20}$(Aminoethylsuccinate)$_{0.10}$]$_n$.
$^1$H NMR Spectrum (CDCl$_3$, ppm):
δ 0.8-1.1 (b, —NHCH(CH(C$\underline{H_3}$)CH$_2$C$\underline{H_3}$)COOCH$_2$CH$_3$),
δ 1.1-1.4 (b, —NHCH(CH(CH$_3$)C$\underline{H_2}$CH$_3$)COOCH$_2$C$\underline{H_3}$),
δ 1.4-1.8 (b, —NHC$\underline{H}$(C$\underline{H}$(CH$_3$)CH$_2$CH$_3$)COOCH$_2$CH$_3$),
δ 2.5-2.7 (b, —NHCH$_2$CH$_2$OCOC$\underline{H_2}$CH$_2$COOH),
δ 2.67-3.2 (b, —NHCH$_2$C$\underline{H_2}$OH, —NH(CH$_2$CH$_2$O)$_{20}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{20}$C$\underline{H_3}$),
δ 3.4-3.9 (b, —NH(C$\underline{H_2}$C$\underline{H_2}$O)$_{20}$CH$_3$, —NHC$\underline{H}$(CH(CH$_3$)CH$_2$CH$_3$)COOC$\underline{H_2}$CH$_3$),
δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$COOH),
Average molecular weight (M$_w$): 14,600

Example 10: Preparation of poly[(isoleucineethylester)$_{1.23}$(aminomethoxypolyethylene Glycol 550)$_{0.68}$(aminoethylglutarate)$_{0.09}$phosphazene]$_n$ Isoleucine ethyl ester hydrochloride (20.76 g), polydichlorophosphazene (10 g), aminoethanol (0.47 g), polyethylene glycol (32.27 g; MW: 550), anhydrous glutarate (8.00 g), and dimethylaminopyridine (8.00 g) were reacted in the same manner as in Example 7 to obtain the final product, [NP(IleOEt)$_{1.23}$(AMPEG550)$_{0.68}$(AminoethylGlutarate)$_{0.09}$]$_n$.
$^1$H NMR Spectrum (CDCl$_3$, ppm):
δ 0.8-1.1 (b, —NHCH(CH(C$\underline{H_3}$)CH$_2$C$\underline{H_3}$)COOCH$_2$CH$_3$),
δ 1.1-1.4 (b, —NHCH(CH(CH$_3$)C$\underline{H_2}$CH$_3$)COOCH$_2$C$\underline{H_3}$),
δ 1.4-1.8 (b, —NHC$\underline{H}$(C$\underline{H}$(CH$_3$)CH$_2$CH$_3$)COOCH$_2$CH$_3$),
δ 2.1-2.32 (b, —NHCH$_2$CH$_2$OCOC$\underline{H_2}$CH$_2$CH$_2$COOH),
δ 2.67-3.2 (b, —NHCH$_2$C$\underline{H_2}$OH, —NH(CH$_2$CH$_2$O)$_{11}$C$\underline{H_3}$),
δ 2.9-3.2 (b, —NHCH$_2$CH$_2$OCOCH$_2$CH$_2$C$\underline{H_2}$COOH),
δ 3.4 (s, —NH(CH$_2$CH$_2$O)$_{11}$C$\underline{H_3}$),
δ 3.4-3.9 (b, —NH(C$\underline{H_2}$C$\underline{H_2}$O)$_{11}$CH$_3$, —NHC$\underline{H}$(CH(CH$_3$)CH$_2$CH$_3$)COOC$\underline{H_2}$CH$_3$),
δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$COOH),
Average molecular weight (M$_w$): 8,400

Example 11: Preparation of poly[(isoleucineethylester)$_{1.38}$(aminomethoxypolyethylene Glycol 750)$_{0.38}$(aminoethylglutarate)$_{0.24}$phosphazene]$_n$ Isoleucine ethyl ester hydrochloride (23.30 g), polydichlorophosphazene (10 g), aminoethanol (1.26 g), polyethylene glycol (24.59 g; MW: 750), anhydrous glutarate (8.00 g), and dimethylaminopyridine (8.00 g) were reacted in the same manner as in Example 10 to obtain the final product, [NP(IleOEt)$_{1.38}$(AMPEG750)$_{0.38}$(AminoethylGlutarate)$_{0.24}$]$_n$.
$^1$H NMR Spectrum (CDCl$_3$, ppm):
δ 0.8-1.1 (b, —NHCH(CH(C$\underline{H_3}$)CH$_2$C$\underline{H_3}$)COOCH$_2$CH$_3$),
δ 1.1-1.4 (b, —NHCH(CH(CH$_3$)C$\underline{H_2}$CH$_3$)COOCH$_2$C$\underline{H_3}$),
δ 1.4-1.8 (b, —NHC$\underline{H}$(C$\underline{H}$(CH$_3$)CH$_2$CH$_3$)COOCH$_2$CH$_3$),
δ 2.1-2.32 (b, —NHCH$_2$CH$_2$OCOC$\underline{H_2}$CH$_2$CH$_2$COOH),
δ 2.67-3.2 (b, —NHCH$_2$C$\underline{H_2}$OH, —NH(CH$_2$CH$_2$O)$_{16}$C$\underline{H_3}$),
δ 2.9-3.2 (b, —NHCH$_2$CH$_2$OCOCH$_2$CH$_2$C$\underline{H_2}$COOH),
δ 3.4 (s, —NH(CH$_2$CH$_2$O)$_{16}$C$\underline{H_3}$),
δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOC$\underline{H_2}$CH$_3$),
δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$COOH),
Average molecular weight (M$_w$): 9,400

Example 12: Preparation of poly[(isoleucineethylester)$_{1.61}$(aminomethoxypolyethylene Glycol 1000)$_{0.22}$(aminoethylglutarate)$_{0.17}$phosphazene]$_n$ Isoleucine ethyl ester hydrochloride (27.18 g), polydichlorophosphazene (10 g), aminoethanol (0.89 g), polyethylene glycol (18.98 g; MW: 1,000), anhydrous glutarate (8.00 g), and dimethylaminopyridine (8.00 g) were reacted in the same manner as in Example 10 to obtain the final product, [NP(IleOEt)$_{1.61}$(AMPEG1000)$_{0.22}$(AminoethylGlutarate)$_{0.17}$]$_n$.
$^1$H NMR Spectrum (CDCl$_3$, ppm):
δ 0.8-1.1 (b, —NHCH(CH(C$\underline{H_3}$)CH$_2$C$\underline{H_3}$)COOCH$_2$CH$_3$),
δ 1.1-1.4 (b, —NHCH(CH(CH$_3$)C$\underline{H_2}$CH$_3$)COOCH$_2$C$\underline{H_3}$),
δ 1.4-1.8 (b, —NHC$\underline{H}$(C$\underline{H}$(CH$_3$)CH$_2$CH$_3$)COOCH$_2$CH$_3$),
δ 2.1-2.32 (b, —NHCH$_2$CH$_2$OCOC$\underline{H_2}$CH$_2$CH$_2$COOH),
δ 2.67-3.2 (b, —NHCH$_2$C$\underline{H_2}$OH, —NH(CH$_2$CH$_2$O)$_{20}$C$\underline{H_3}$),
δ 2.9-3.2 (b, —NHCH$_2$CH$_2$OCOCH$_2$CH$_2$C$\underline{H_2}$COOH),
δ 3.4 (s, —NH(CH$_2$CH$_2$O)$_{20}$C$\underline{H_3}$),
δ 3.4-3.9 (b, —NH(C$\underline{H_2}$C$\underline{H_2}$O)$_{20}$CH$_3$, —NHC$\underline{H}$(CH(CH$_3$)CH$_2$CH$_3$)COOC$\underline{H_2}$CH$_3$),
δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$COOH),
Average molecular weight (M$_w$): 17,500

Example 13: Preparation of poly[(isoleucineethylester)$_{1.48}$(aminomethoxypolyethylene Glycol 750)$_{0.34}$(aminoethylglutarate beta-cyclodextrin)$_{0.18}$phosphazene]$_n$ Isoleucine ethyl ester hydrochloride (24.99 g), polydichlorophosphazene (10 g), aminoethanol (0.94 g), polyethylene glycol (22.00 g; MW: 750), anhydrous glutarate (8.00 g), and dimethylaminopyridine (8.00 g) were reacted in the same manner as in Example 10 to obtain a polymer, and the thus-obtained polymer was reacted by adding amino beta-cyclodextrin (10 g) to obtain the final product, [NP(IleOEt)$_{1.48}$(AMPEG750)$_{0.34}$(AminoethylGlutaricBeta-CD)$_{0.18}$]$_n$.

$^1$H NMR Spectrum (CDCl$_3$, ppm):
- δ 0.8-1.1 (b, —NHCH(CH(C$\underline{H_3}$)CH$_2$C$\underline{H_3}$)COOCH$_2$CH$_3$),
- δ 1.1-1.4 (b, —NHCH(CH(CH$_3$)C$\underline{H_2}$CH$_3$)COOCH$_2$C$\underline{H_3}$),
- δ 1.4-1.8 (b, —NHC$\underline{H}$(CH(CH$_3$)CH$_2$CH$_3$)COOCH$_2$CH$_3$),
- δ 2.1-2.32 (b, —NHCH$_2$CH$_2$OCOC$\underline{H_2}$CH$_2$CH$_2$COOH),
- δ 2.67-3.2 (b, —NHCH$_2$C$\underline{H_2}$OH, —NH(CH$_2$CH$_2$O)$_{16}$C$\underline{H_3}$),
- δ 2.9-3.2 (b, —NHCH$_2$CH$_2$OCOCH$_2$CH$_2$C$\underline{H_2}$COOH),
- δ 3.4 (s, —NH(CH$_2$CH$_2$O)$_{16}$C$\underline{H_3}$),
- δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
- δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH),
- δ 4.7-4.8(b, —NHC$\underline{H_2}$Beta-cyclodextrin), Average molecular weight (M$_w$): 7,500

Example 14: Preparation of poly[(isoleucineethylester)$_{1.51}$(aminomethoxypolyethylene Glycol 750)$_{0.25}$(aminoethyladipate)$_{0.24}$phosphazene]$_n$ Isoleucine ethyl ester hydrochloride (25.49 g), polydichlorophosphazene (10 g), aminoethanol (1.26 g), polyethylene glycol (22.00 g; MW: 750), anhydrous adipate (7.00 g), and dimethylaminopyridine (7.00 g) were reacted in the same manner as in Example 10 to obtain the final product, [NP(IleOEt)$_{1.51}$(AMPEG750)$_{0.25}$(AminoethylAdipate)$_{0.24}$]$_n$.

$^1$H NMR Spectrum (CDCl$_3$, ppm):
- δ 0.8-1.1 (b, —NHCH(CH(C$\underline{H_3}$)CH$_2$C$\underline{H_3}$)COOCH$_2$CH$_3$),
- δ 1.1-1.4 (b, —NHCH(CH(CH$_3$)C$\underline{H_2}$CH$_3$)COOCH$_2$C$\underline{H_3}$),
- δ 1.4-1.8 (b, —NHC$\underline{H}$(CH(CH$_3$)CH$_2$CH$_3$)COOCH$_2$CH$_3$),
- δ 1.52-1.64 (b, —NHCH$_2$CH$_2$OCOCH$_2$C$\underline{H_2}$C$\underline{H_2}$CH$_2$COOH),
- δ 2.3-2.32 (b, —NHCH$_2$CH$_2$OCOC$\underline{H_2}$CH$_2$CH$_2$C$\underline{H_2}$COOH),
- δ 2.67-3.2 (b, —NHCH$_2$C$\underline{H_2}$OH, —NH(CH$_2$CH$_2$O)$_{16}$C$\underline{H_3}$),
- δ 3.4 (s, —NH(CH$_2$CH$_2$O)$_{16}$C$\underline{H_3}$),
- δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
- δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH), Average molecular weight (M$_w$): 4,530

Example 15: Preparation of poly[(isoleucineethylester)$_{1.18}$(aminomethoxypolyethylene Glycol 550)$_{0.72}$(aminoethylsulfate)$_{0.10}$phosphazene]$_n$ Isoleucine ethyl ester hydrochloride (19.92 g), polydichlorophosphazene (10 g), aminoethanol (0.52 g), polyethylene glycol (34.17 g; MW: 550), and a sulfur trioxide pyridine complex (5.00 g) were reacted in the same manner as in Example 10 to obtain the final product, [NP(IleOEt)$_{1.18}$(AMPEG550)$_{0.72}$(Aminoethylsulfate)$_{0.10}$]$_n$.

$^1$H NMR Spectrum (CDCl$_3$, ppm):
- δ 0.8-1.1 (b, —NHCH(CH(C$\underline{H_3}$)CH$_2$C$\underline{H_3}$)COOCH$_2$CH$_3$),
- δ 1.1-1.4 (b, —NHCH(CH(CH$_3$)C$\underline{H_2}$CH$_3$)COOCH$_2$C$\underline{H_3}$),
- δ 1.4-1.8 (b, —NHC$\underline{H}$(CH(CH$_3$)CH$_2$CH$_3$)COOCH$_2$CH$_3$),
- δ 2.67-3.2 (b, —NHCH$_2$C$\underline{H_2}$SO$_4$, —NH(CH$_2$CH$_2$O)$_{11}$C$\underline{H_3}$),
- δ 3.4 (s, —NH(CH$_2$CH$_2$O)$_{11}$C$\underline{H_3}$),
- δ 3.4-3.9 (b, —NH(C$\underline{H_2}$C$\underline{H_2}$O)$_{11}$CH$_3$, —NHC$\underline{H}$(CH(CH$_3$)CH$_2$CH$_3$)COOC$\underline{H_2}$CH$_3$),
- δ 3.9-4.3 (b, —NHCH(CH(CH$_3$)CH$_2$CH$_3$)COOC$\underline{H_2}$CH$_3$), Average molecular weight (M$_w$): 8,600

Example 16: Preparation of poly[(isoleucineethylester)$_{1.40}$(aminomethoxypolyethylene Glycol 750)$_{0.30}$(aminoethylsulfate)$_{0.30}$phosphazene]$_n$ Isoleucine ethyl ester hydrochloride (23.63 g), polydichlorophosphazene (10 g), aminoethanol (1.58 g), polyethylene glycol (19.41 g; MW: 750), and a sulfur trioxide pyridine complex (8.00 g) were reacted in the same manner as in Example 15 to obtain the final product, [NP(IleOEt)$_{1.40}$(AMPEG750)$_{0.30}$(Aminoethylsulfate)$_{0.30}$]$_n$.

$^1$H NMR Spectrum (CDCl$_3$, ppm):
- δ 0.8-1.1 (b, —NHCH(CH(C$\underline{H_3}$)CH$_2$C$\underline{H_3}$)COOCH$_2$CH$_3$),
- δ 1.1-1.4 (b, —NHCH(CH(CH$_3$)C$\underline{H_2}$CH$_3$)COOCH$_2$C$\underline{H_3}$),
- δ 1.4-1.8 (b, —NHC$\underline{H}$(CH(CH$_3$)CH$_2$CH$_3$)COOCH$_2$CH$_3$),
- δ 2.67-3.2 (b, —NHCH$_2$C$\underline{H_2}$SO$_4$, —NH(CH$_2$CH$_2$O)$_{16}$C$\underline{H_3}$),
- δ 3.4 (s, —NH(CH$_2$CH$_2$O)$_{16}$C$\underline{H_3}$),
- δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
- δ 3.9-4.3 (b, —NHCH(CH(CH$_3$)CH$_2$CH$_3$)COOC$\underline{H_2}$CH$_3$), Average molecular weight (M$_w$): 7,700

Example 17: Preparation of poly[(isoleucineethylester)$_{1.40}$(aminomethoxypolyethylene Glycol 750)$_{0.30}$(aminoethylmethacrylate)$_{0.30}$phosphazene]$_n$ Isoleucine ethyl ester hydrochloride (23.63 g), polydichlorophosphazene (10 g), polyethylene glycol (19.41 g; MW: 750), and amino methacrylate hydrogen chloride (3.00 g), which was dissolved in dimethyl formamide, were reacted in the same manner as in Example 1 to obtain the final product, [NP(IleOEt)$_{1.40}$(AMPEG750)$_{0.30}$(AminoethylMethacrylate)$_{0.30}$]$_n$.

$^1$H NMR Spectrum (CDCl$_3$, ppm):
- δ 0.8-1.1 (b, —NHCH(CH(C$\underline{H_3}$)CH$_2$C$\underline{H_3}$)COOCH$_2$CH$_3$),
- δ 1.1-1.4 (b, —NHCH(CH(CH$_3$)C$\underline{H_2}$CH$_3$)COOCH$_2$C$\underline{H_3}$),
- δ 1.4-1.8 (b, —NHC$\underline{H}$(CH(CH$_3$)CH$_2$CH$_3$)COOCH$_2$CH$_3$),
- δ 1.9 (s, —NHCH$_2$CH$_2$O$_2$C(C$\underline{H_3}$)C=CH$_2$),
- δ 3.4 (s, —NH(CH$_2$CH$_2$O)$_{16}$C$\underline{H_3}$),
- δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
- δ 3.9-4.3 (b, —NHCH(CH(CH$_3$)CH$_2$CH$_3$)COOC$\underline{H_2}$CH$_3$),
- δ 5.5 (s, —NHCH$_2$CH$_2$O$_2$C(CH$_3$)C=C$\underline{H_2}$),
- δ 6.1 (s, —NHCH$_2$CH$_2$O$_2$C(CH$_3$)C=C$\underline{H_2}$), Average molecular weight (M$_w$): 14,500

Example 18: Preparation of poly[(isoleucineethylester)$_{1.11}$(aminomethoxypolyethylene Glycol 550)$_{0.75}$(aminoethylacrylate)$_{0.14}$phosphazene]$_n$ Isoleucine ethyl ester hydrochloride (18.74 g), polydichlorophosphazene (10 g), aminoethanol (0.73 g), polyethylene glycol (35.59 g; MW: 550), and acrylate (3.00 g), which was dissolved in THF, were reacted in the same manner as in Example 10 to obtain the final jproduct, [NP(IleOEt)$_{1.11}$(AMPEG550)$_{0.75}$(Aminoethyl-Acrylate)$_{0.14}$]$_n$.

$^1$H NMR Spectrum (CDCl$_3$, ppm):
δ  0.8-1.1  (b,  —NHCH(CH(C$\underline{H_3}$)CH$_2$C$\underline{H_3}$)COOCH$_2$CH$_3$),
δ  1.1-1.4  (b,  —NHCH(CH(CH$_3$)C$\underline{H_2}$CH$_3$)COOCH$_2$C$\underline{H_3}$),
δ  1.4-1.8  (b,  —NHC$\underline{H}$(CH(CH$_3$)CH$_2$CH$_3$)COOCH$_2$CH$_3$),
δ 1.9 (s, —NHCH$_2$CH$_2$O$_2$C(C$\underline{H_3}$)C═CH$_2$),
δ 3.4 (s, —NH(CH$_2$CH$_2$O)$_{11}$C$\underline{H_3}$),
δ 3.4-3.9 (b, —NH(C$\underline{H_2}$C$\underline{H_2}$O)$_{11}$CH$_3$, —NHC$\underline{H}$(CH(CH$_3$)CH$_2$CH$_3$)COOC$\underline{H_2}$CH$_3$),
δ  3.9-4.3  (b,  —NHCH(CH(CH$_3$)CH$_2$CH$_3$)COOC$\underline{H_2}$CH$_3$),
δ 5.5-6.5 (s, —NHCH$_2$CH$_2$O$_2$C═C$\underline{H}$),
Average molecular weight ($M_w$): 26,500

Example 19: Preparation of poly[(isoleucineethylester)$_{1.55}$(aminomethoxypolyethylene Glycol 750)$_{0.38}$(aminoethylsuccinateimidazole)$_{0.07}$phosphazene]$_n$ Isoleucine ethyl ester hydrochloride (26.17 g), polydichlorophosphazene (10 g), aminoethanol (0.36 g), polyethylene glycol (24.59 g; MW: 750), anhydrous succinate (4.00 g), dimethylaminopyridine (4.00 g), diisopropyl carbodiimidazole (15.00 g), hydroxysuccinimide (15.00 g), and 1-(3-aminopropylimidazole) (10.00 g), which was dissolved in THF, were reacted in the same manner as in Example 10 to obtain the final product, [NP(IleOEt)$_{1.55}$(AMPEG750)$_{0.38}$(Aminoethylsuccinatemidazole)$_{0.07}$]$_n$.

$^1$H NMR Spectrum (CDCl$_3$, ppm):
δ  0.8-1.1  (b,  —NHCH(CH(C$\underline{H_3}$)CH$_2$C$\underline{H_3}$)COOCH$_2$CH$_3$),
δ  1.1-1.4  (b,  —NHCH(CH(CH$_3$)C$\underline{H_2}$CH$_3$)COOCH$_2$C$\underline{H_3}$),
δ  1.4-1.8  (b,  —NHC$\underline{H}$(CH(CH$_3$)CH$_2$CH$_3$)COOCH$_2$CH$_3$),
δ 2.5-2.7 (b, —NHCH$_2$CH$_2$OCOC$\underline{H_2}$CH$_2$COOH),
δ 2.67-3.2 (b, —NHCH$_2$C$\underline{H_2}$OH, —NH(CH$_2$CH$_2$O)$_{16}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{16}$C$\underline{H_3}$),
δ  3.4-3.9  (b,  —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$COOH),
δ 6.8-7.8 (b, —NHCH$_2$CH$_2$OCOC$\underline{H}$CH$_2$CONH—Imi),
Average molecular weight ($M_w$): 9,700

Example 20: Preparation of poly[(isoleucineethylester)$_{1.51}$(aminomethoxypolyethylene Glycol 750)$_{0.40}$(aminoethylsuccinatepolypeptide)$_{0.09}$phosphazene]$_n$ Isoleucine ethyl ester hydrochloride (25.15 g), polydichlorophosphazene (10 g), aminoethanol (0.47 g), polyethylene glycol (27.18 g; MW: 750), anhydrous succinate (4.00 g), hexylamine (4.00 g), and a polypeptide (3.00 g), which was dissolved in dimethyl sulfur monoxide, were reacted in the same manner as in Example 10 to obtain the final product, [NP(IleOEt)$_{1.51}$(AMPEG750)$_{0.40}$(AminoethylsuccinateCRRRRHHHHHHGGGGRGDS)$_{0.09}$]$_n$.

The polypeptide was quantified using an amino acid quantification method.

$^1$H NMR Spectrum (CDCl$_3$, ppm):
δ  0.8-1.1  (b,  —NHCH(CH(C$\underline{H_3}$)CH$_2$C$\underline{H_3}$)COOCH$_2$CH$_3$),
δ  1.1-1.4  (b,  —NHCH(CH(CH$_3$)C$\underline{H_2}$CH$_3$)COOCH$_2$C$\underline{H_3}$),
δ  1.4-1.8  (b,  —NHC$\underline{H}$(CH(CH$_3$)CH$_2$CH$_3$)COOCH$_2$CH$_3$),
δ 2.5-2.7 (b, —NHCH$_2$CH$_2$OCOCH$_2$CH$_2$COOH),
δ 2.67-3.2 (b, —NHCH$_2$C$\underline{H_2}$OH, —NH(CH$_2$CH$_2$O)$_{16}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{16}$C$\underline{H_3}$),
δ  3.4-3.9  (b,  —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$COOH),
Average molecular weight ($M_w$): 13,700

Comparative Example 1: Preparation of poly[(isoleucineethylester)$_{1.12}$(aminomethoxypolyethylene Glycol 550)$_{0.85}$(ethyl-2-(O-glycyl)lactate)$_{0.03}$phosphazene]$_n$ Isoleucine ethyl ester hydrochloride (19.75 g), polydichlorophosphazene (10 g), ethyl-2-(O-glycyl)lactate ammonium oxalate (0.52 g), and polyethylene glycol (37.96 g; MW: 550) were reacted in the same manner as in Example 1 to obtain the final product, [NP(IleOEt)$_{1.12}$(AMPEG550)$_{0.85}$(GyLacOEt)$_{0.03}$]$_n$.

$^1$H NMR Spectrum (CDCl$_3$, ppm):
δ  0.8-1.1  (b,  —NHCH(CH(C$\underline{H_3}$)CH$_2$C$\underline{H_3}$)COOCH$_2$CH$_3$),
δ  1.1-1.4  (b,  —NHCH(CH(CH$_3$)C$\underline{H_2}$CH$_3$)COOCH$_2$C$\underline{H_3}$),
δ 1.3-1.5 (b, —NHCH$_2$COOCH(CH$_3$)COOCH$_2$C$\underline{H_3}$),
δ  1.4-1.8  (b,  —NHC$\underline{H}$(CH(CH$_3$)CH$_2$CH$_3$)COOCH$_2$CH$_3$),
δ 1.6-1.7 (b, —NHCH$_2$COOCH(C$\underline{H_3}$)COOCH$_2$CH$_3$),
δ 2.67-3.2 (b, —NH(CH$_2$CH$_2$O)$_{11}$C$\underline{H_3}$),
δ 3.4 (s, —NH(CH$_2$CH$_2$O)$_{11}$C$\underline{H_3}$),
δ  3.4-3.9  (b,  —NH(C$\underline{H_2}$C$\underline{H_2}$O)$_{11}$CH$_3$, —NHC$\underline{H}$(CH(CH$_3$)CH$_2$CH$_3$)COOCH$_2$CH$_3$),
δ  3.9-4.3  (b,  —NHCH(CH(CH$_3$)CH$_2$CH$_3$)COOC$\underline{H_2}$CH$_3$),
δ 4.0-4.4 (b, —NHC$\underline{H_2}$COOCH(CH$_3$)COOCH$_2$CH$_3$),
δ 5.2-5.4 (b, —NHCH$_2$COOC$\underline{H}$(CH$_3$)COOC$\underline{H_2}$CH$_3$),
Average molecular weight ($M_w$): 69,000

Comparative Example 2: Preparation of poly[(isoleucineethylester)$_{1.32}$(aminomethoxypolyethylene Glycol 750)$_{0.65}$(ethyl-2-(O-glycyl)lactate)$_{0.03}$phosphazene]$_n$ Isoleucine ethyl ester hydrochloride (22.28 g), polydichlorophosphazene (10 g), ethyl-2-(O-glycyl)lactate ammonium oxalate (0.52 g), and polyethylene glycol (42.06 g; MW: 750) were reacted in the same manner as in Example 1 to obtain the final product, [NP(IleOEt)$_{1.32}$(AMPEG750)$_{0.65}$(GyLacOEt)$_{0.03}$]$_n$.

$^1$H NMR Spectrum (CDCl$_3$, ppm):
δ  0.8-1.1  (b,  —NHCH(CH(C$\underline{H_3}$)CH$_2$C$\underline{H_3}$)COOCH$_2$CH$_3$),
δ  1.1-1.4  (b,  —NHCH(CH(CH$_3$)C$\underline{H_2}$CH$_3$)COOCH$_2$C$\underline{H_3}$),
δ 1.3-1.5 (b, —NHCH$_2$COOCH(CH$_3$)COOCH$_2$C$\underline{H_3}$),
δ  1.4-1.8  (b,  —NHC$\underline{H}$(C$\underline{H}$(CH$_3$)C$\underline{H_2}$CH$_3$)COOCH$_2$CH$_3$),
δ 1.6-1.7 (b, —NHCH$_2$COOCH(C$\underline{H_3}$)COOCH$_2$CH$_3$),
δ 2.67-3.2 (b, —NH(CH$_2$CH$_2$O)$_{16}$C$\underline{H_3}$),
δ 3.4 (s, —NH(CH$_2$CH$_2$O)$_{16}$C$\underline{H_3}$),
δ  3.4-3.9  (b,  —NH(C$\underline{H_2}$C$\underline{H_2}$O)$_{16}$CH$_3$, —NHC$\underline{H}$(CH(CH$_3$)CH$_2$CH$_3$)COOC$\underline{H_2}$C$\underline{H_3}$),
δ  3.9-4.3  (b,  —NHCH(CH(CH$_3$)CH$_2$CH$_3$)COOC$\underline{H_2}$CH$_3$),
δ 4.0-4.4 (b, —NHC$\underline{H_2}$COOCH(CH$_3$)COOC$\underline{H_2}$CH$_3$),
δ 5.2-5.4 (b, —NHC$\underline{H_2}$COOC$\underline{H}$(CH$_3$)COOC$\underline{H_2}$CH$_3$),
Average molecular weight (M$_w$): 58,000

Comparative Example 3: Preparation of poly[(iso-leucineethylester)$_{1.30}$(aminomethoxypolyethylene Glycol 750)$_{0.42}$(aminoethanol)$_{0.28}$phosphazene]$_n$ Isoleucine ethyl ester hydrochloride (21.95 g), polydichlorophosphazene (10 g), aminoethanol (1.58 g), and polyethylene glycol (25.88 g; MW: 750) were reacted in the same manner as in Example 1, except that THF was used instead of anhydrous acetonitrile when aminoethanol was added, to obtain the final product, [NP(IleOEt)$_{1.30}$(AMPEG750)$_{0.42}$(Aminoethanol)$_{0.28}$]$_n$.

$^1$H NMR Spectrum (CDCl$_3$, ppm):
δ  0.8-1.1  (b,  —NHCH(CH(C$\underline{H_3}$)CH$_2$C$\underline{H_3}$)COOCH$_2$CH$_3$),
δ  1.1-1.4  (b,  —NHCH(CH(CH$_3$)C$\underline{H_2}$CH$_3$)COOCH$_2$C$\underline{H_3}$),
δ  1.4-1.8  (b,  —NHC$\underline{H}$(C$\underline{H}$(CH$_3$)CH$_2$CH$_3$)COOCH$_2$CH$_3$),
δ  2.67-3.2  (b,  —NHCH$_2$C$\underline{H_2}$OH, —NH(CH$_2$CH$_2$O)$_{11}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{11}$C$\underline{H_3}$),
δ  3.4-3.9  (b,  —NH(C$\underline{H_2}$C$\underline{H_2}$O)$_{11}$CH$_3$, —NHC$\underline{H}$(CH(CH$_3$)CH$_2$CH$_3$)COOC$\underline{H_2}$C$\underline{H_3}$),
δ  3.9-4.3  (b,  —NHCH(CH(CH$_3$)CH$_2$CH$_3$)COOC$\underline{H_2}$CH$_3$),
Average molecular weight (M$_w$): 5,900

Comparative Example 4: Preparation of poly[(iso-leucineethylester)$_{1.07}$(aminomethoxypolyethylene Glycol 550)$_{0.81}$(aminoethylsuccinate)$_{0.12}$phosphazene]$_n$ Isoleucine ethyl ester hydrochloride (18.06 g), polydichlorophosphazene (10 g), aminoethanol (0.63 g), polyethylene glycol (38.44 g; MW: 550), anhydrous succinate (4.00 g), and dimethylaminopyridine (4.00 g) were reacted in the same manner as in Example 4 to obtain the final product, [NP(IleOEt)$_{1.07}$(AMPEG550)$_{0.81}$(Aminoethylsuccinate)$_{0.12}$]$_n$.

$^1$H NMR Spectrum (CDCl$_3$, ppm):
δ  0.8-1.1  (b,  —NHCH(CH(C$\underline{H_3}$)CH$_2$C$\underline{H_3}$)COOCH$_2$CH$_3$),
δ  1.1-1.4  (b,  —NHCH(CH(CH$_3$)C$\underline{H_2}$CH$_3$)COOCH$_2$C$\underline{H_3}$),
δ  1.4-1.8  (b,  —NHC$\underline{H}$(C$\underline{H}$(CH$_3$)CH$_2$CH$_3$)COOCH$_2$CH$_3$),
δ 2.5-2.7 (b, —NHCH$_2$CH$_2$OCOC$\underline{H_2}$CH$_2$COOH),
δ  2.67-3.2  (b,  —NHCH$_2$C$\underline{H_2}$OH, —NH(CH$_2$CH$_2$O)$_{11}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{11}$C$\underline{H_3}$),
δ  3.4-3.9  (b,  —NH(C$\underline{H_2}$C$\underline{H_2}$O)$_{11}$CH$_3$, —NHC$\underline{H}$(CH(CH$_3$)CH$_2$CH$_3$)COOCH$_2$CH$_3$),
δ  3.9-4.3  (b,  —NHCH(CH(CH$_3$)CH$_2$CH$_3$)COOC$\underline{H_2}$CH$_3$, —NHCH$_2$C$\underline{H_2}$OCOCH$_2$CH$_2$COOH),
Average molecular weight (M$_w$): 13,200

Comparative Example 5: Preparation of poly[(iso-leucineethylester)$_{1.39}$(aminomethoxypolyethylene Glycol 750)$_{0.41}$(aminoethylsuccinate)$_{0.20}$phosphazene]$_n$ Isoleucine ethyl ester hydrochloride (23.47 g), polydichlorophosphazene (10 g), aminoethanol (1.05 g), polyethylene glycol (26.53 g; MW: 750), anhydrous succinate (4.00 g), and dimethylaminopyridine (4.00 g) were reacted in the same manner as in Example 4 to obtain the final product, [NP(IleOEt)$_{1.39}$(AMPEG750)$_{0.41}$(Aminoethylsuccinate)$_{0.20}$]$_n$.

$^1$H NMR Spectrum (CDCl$_3$, ppm):
δ  0.8-1.1  (b,  —NHCH(CH(C$\underline{H_3}$)CH$_2$C$\underline{H_3}$)COOCH$_2$CH$_3$),
δ  1.1-1.4  (b,  —NHCH(CH(CH$_3$)C$\underline{H_2}$CH$_3$)COOCH$_2$C$\underline{H_3}$),
δ  1.4-1.8  (b,  —NHC$\underline{H}$(C$\underline{H}$(CH$_3$)CH$_2$CH$_3$)COOCH$_2$CH$_3$),
δ 2.5-2.7 (b, —NHCH$_2$CH$_2$OCOC$\underline{H_2}$CH$_2$COOH),
δ  2.67-3.2  (b,  —NHCH$_2$C$\underline{H_2}$OH, —NH(CH$_2$CH$_2$O)$_{16}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{16}$C$\underline{H_3}$),
δ  3.4-3.9  (b,  —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ  3.9-4.3  (b,  —NHCH(CH(CH$_3$)CH$_2$CH$_3$)COOC$\underline{H_2}$CH$_3$, —NHCH$_2$C$\underline{H_2}$OCOCH$_2$CH$_2$COOH),
Average molecular weight (M$_w$): 41,200

Comparative Example 6: Preparation of poly[(iso-leucineethylester)$_{1.05}$(aminomethoxypolyethylene Glycol 550)$_{0.81}$(aminoethylglutarate)$_{0.14}$phosphazene]$_n$ Isoleucine ethyl ester hydrochloride (17.72 g), polydichlorophosphazene (10 g), aminoethanol (0.73 g), polyethylene glycol (38.44 g; MW: 550), anhydrous glutarate (7.00 g), and dimethylaminopyridine (7.00 g) were reacted in the same manner as in Example 7 to obtain the final product, [NP(IleOEt)$_{1.05}$(AMPEG550)$_{0.81}$(AminoethylGlutarate)$_{0.14}$]$_n$.

$^1$H NMR Spectrum (CDCl$_3$, ppm):
δ  0.8-1.1  (b,  —NHCH(CH(C$\underline{H_3}$)CH$_2$C$\underline{H_3}$)COOCH$_2$CH$_3$),
δ  1.1-1.4  (b,  —NHCH(CH(CH$_3$)C$\underline{H_2}$CH$_3$)COOCH$_2$C$\underline{H_3}$),
δ  1.4-1.8  (b,  —NHC$\underline{H}$(C$\underline{H}$(CH$_3$)CH$_2$CH$_3$)COOCH$_2$CH$_3$),
δ 2.1-2.32 (b, —NHCH$_2$CH$_2$OCOCH$_2$CH$_2$C$\underline{H_2}$COOH),
δ  2.67-3.2  (b,  —NHCH$_2$C$\underline{H_2}$OH, —NH(CH$_2$CH$_2$O)$_{11}$C$\underline{H_3}$),
δ 2.9-3.2 (b, —NHCH$_2$CH$_2$OCOCH$_2$C$\underline{H_2}$COOH),
δ 3.4 (s, —NH(CH$_2$CH$_2$O)$_{11}$C$\underline{H_3}$),
δ  3.4-3.9  (b,  —NH(C$\underline{H_2}$C$\underline{H_2}$O)$_{11}$CH$_3$, —NHC$\underline{H}$(CH(CH$_3$)CH$_2$CH$_3$)COOCH$_2$CH$_3$), δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH),
Average molecular weight (M$_w$): 7,900

Comparative Example 7: Preparation of poly[(isoleucineethylester)$_{1.32}$(aminomethoxypolyethylene Glycol 750)$_{0.42}$(aminoethylglutarate)$_{0.26}$phosphazene]$_n$ Isoleucine ethyl ester hydrochloride (22.28 g), polydichlorophosphazene (10 g), aminoethanol (1.58 g), polyethylene glycol (24.59 g; MW: 750), anhydrous glutarate (8.00 g), and dimethylaminopyridine (8.00 g) were reacted in the same manner as in Example 7 to obtain the final product, [NP(IleOEt)$_{0.32}$(AMPEG750)$_{0.42}$(AminoethylGlutarate)$_{0.26}$]$_n$.
$^1$H NMR Spectrum (CDCl$_3$, ppm):
 δ   0.8-1.1   (b,   —NHCH(CH(C$\underline{H_3}$)CH$_2$C$\underline{H_3}$) COOCH$_2$CH$_3$),
 δ   1.1-1.4   (b,   —NHCH(CH(CH$_3$)C$\underline{H_2}$CH$_3$) COOCH$_2$C$\underline{H_3}$),
 δ   1.4-1.8   (b,   —NHC$\underline{H}$(C$\underline{H}$(CH$_3$)CH$_2$CH$_3$) COOCH$_2$CH$_3$),
δ 2.1-2.32 (b, —NHCH$_2$CH$_2$OCOC$\underline{H_2}$CH$_2$CH$_2$COOH),
δ 2.67-3.2 (b, —NHCH$_2$C$\underline{H_2}$OH, —NH(CH$_2$CH$_2$O)$_{16}$C$\underline{H_3}$),
δ 2.9-3.2 (b, —NHCH$_2$CH$_2$OCOCH$_2$CH$_2$C$\underline{H_2}$COOH),
δ 3.4 (s, —NH(CH$_2$CH$_2$O)$_{16}$C$\underline{H_3}$),
δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOC$\underline{H_2}$C$\underline{H_3}$),
δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH),
Average molecular weight (M$_w$): 5,800

Comparative Example 8: Preparation of poly[(isoleucineethylester)$_{1.61}$(aminomethoxypolyethylene Glycol 1000)$_{0.34}$(aminoethylglutarate)$_{0.05}$phosphazene]$_n$ Isoleucine ethyl ester hydrochloride (29.54 g), polydichlorophosphazene (10 g), aminoethanol (0.26 g), polyethylene glycol (17.25 g; MW: 1,000), anhydrous glutarate (8.00 g), and dimethylaminopyridine (8.00 g) were reacted in the same manner as in Example 7 to obtain the final product, [NP(IleOEt)$_{1.61}$(AMPEG1000)$_{0.34}$(AminoethylGlutarate)$_{0.05}$]$_n$.
$^1$H NMR Spectrum (CDCl$_3$, ppm):
 δ   0.8-1.1   (b,   —NHCH(CH(C$\underline{H_3}$)CH$_2$C$\underline{H_3}$) COOCH$_2$CH$_3$),
 δ   1.1-1.4   (b,   —NHCH(CH(CH$_3$)C$\underline{H_2}$CH$_3$) COOCH$_2$C$\underline{H_3}$),
 δ   1.4-1.8   (b,   —NHC$\underline{H}$(C$\underline{H}$(CH$_3$)CH$_2$CH$_3$) COOCH$_2$CH$_3$),
δ 2.1-2.32 (b, —NHCH$_2$CH$_2$OCOC$\underline{H_2}$CH$_2$CH$_2$COOH),
δ 2.67-3.2 (b, —NHCH$_2$C$\underline{H_2}$OH, —NH(CH$_2$CH$_2$O)$_{20}$C$\underline{H_3}$),
δ 2.9-3.2 (b, —NHCH$_2$CH$_2$OCOCH$_2$CH$_2$C$\underline{H_2}$COOH),
δ 3.4 (s, —NH(CH$_2$CH$_2$O)$_{20}$C$\underline{H_3}$),
δ 3.4-3.9 (b, —NH(C$\underline{H_2}$C$\underline{H_2}$O)$_{20}$CH$_3$, —NHC$\underline{H}$(CH(CH$_3$)CH$_2$CH$_3$)COOC$\underline{H_2}$C$\underline{H_3}$),
δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH),
Average molecular weight (M$_w$): 9,800

Comparative Example 9: Preparation of poly[(isoleucineethylester)$_{1.33}$(aminomethoxypolyethylene Glycol 750)$_{0.47}$(aminoethylglutaratebeta-cyclodextrin)$_{0.20}$phosphazene]$_n$ Isoleucine ethyl ester hydrochloride (22.45 g), polydichlorophosphazene (10 g), aminoethanol (1.05 g), polyethylene glycol (30.41 g; MW: 750), anhydrous glutarate (8.00 g), and dimethylaminopyridine (8.00 g) were reacted in the same manner as in Example 10 to obtain a polymer, and the thus-obtained polymer was reacted by adding amino beta-cyclodextrin (16.00 g) to obtain the final product, [NP(IleOEt)$_{1.33}$(AMPEG750)$_{0.47}$(AminoethylGlutaricBeta-CD)$_{0.20}$]$_n$.
$^1$H NMR Spectrum (CDCl$_3$, ppm):
 δ   0.8-1.1   (b,   —NHCH(CH(C$\underline{H_3}$)CH$_2$CH$_3$) COOCH$_2$CH$_3$),
 δ   1.1-1.4   (b,   —NHCH(CH(CH$_3$)C$\underline{H_2}$CH$_3$) COOCH$_2$CH$_3$),
 δ   1.4-1.8   (b,   —NHC$\underline{H}$(CH(CH$_3$)CH$_2$CH$_3$) COOCH$_2$CH$_3$),
δ 2.1-2.32 (b, —NHCH$_2$CH$_2$OCOC$\underline{H_2}$CH$_2$CH$_2$COOH),
δ 2.67-3.2 (b, —NHCH$_2$C$\underline{H_2}$OH, —NH(CH$_2$CH$_2$O)$_{16}$C$\underline{H_3}$),
δ 2.9-3.2 (b, —NHCH$_2$CH$_2$OCOCH$_2$CH$_2$C$\underline{H_2}$COOH),
δ 3.4 (s, —NH(CH$_2$CH$_2$O)$_{16}$C$\underline{H_3}$),
δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.9-4.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH),
δ 4.7-4.8 (b, —NHC$\underline{H_2}$Beta-cyclodextrin),
Average molecular weight (M$_w$): 15,500

Comparative Example 10: Preparation of poly[(isoleucineethylester)$_{1.4}$(aminomethoxypolyethylene Glycol 750)$_{0.42}$(aminoethyladipate)$_{0.10}$phosphazene]$_n$ Isoleucine ethyl ester hydrochloride (24.99 g), polydichlorophosphazene (10 g), aminoethanol (0.52 g), polyethylene glycol (27.18 g; MW: 750), anhydrous adipate (8.00 g), and dimethylaminopyridine (8.00 g) were reacted in the same manner as in Example 10 to obtain the final product, [NP(IleOEt)$_{1.48}$(AMPEG750)$_{0.42}$(AminoethylAdipate)$_{0.10}$]$_n$.
$^1$H NMR Spectrum (CDCl$_3$, ppm):
 δ   0.8-1.1   (b,   —NHCH(CH(C$\underline{H_3}$)CH$_2$C$\underline{H_3}$) COOCH$_2$CH$_3$),
 δ   1.1-1.4   (b,   —NHCH(CH(CH$_3$)C$\underline{H_2}$CH$_3$) COOCH$_2$C$\underline{H_3}$),
 δ   1.4-1.8   (b,   —NHC$\underline{H}$(C$\underline{H}$(CH$_3$)CH$_2$CH$_3$) COOCH$_2$CH$_3$),
 δ   1.52-1.64   (b, —NHCH$_2$CH$_2$OCOCH$_2$C$\underline{H_2}$C$\underline{H_2}$CH$_2$COOH),
 δ   2.3-2.32   (b, —NHCH$_2$CH$_2$OCOC$\underline{H_2}$CH$_2$CH$_2$C$\underline{H_2}$COOH),
δ 2.67-3.2 (b, —NHCH$_2$C$\underline{H_2}$OH, —NH(CH$_2$CH$_2$O)$_{16}$C$\underline{H_3}$),
δ 3.4 (s, —NH(CH$_2$CH$_2$O)$_{16}$C$\underline{H_3}$),
δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.94.3 (b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH),
Average molecular weight (M$_w$): 4,600

Comparative Example 11: Preparation of poly[(isoleucineethylester)$_{1.49}$(aminomethoxypolyethylene Glycol 750)$_{0.44}$(aminoethylsulfate)$_{0.07}$phosphazene]$_n$ Isoleucine ethyl ester hydrochloride (25.15 g), polydichlorophosphazene (10 g), aminoethanol (0.36 g), polyethylene glycol (28.47 g; MW: 750), and a sulfur trioxide pyridine complex (5.00 g) were reacted in the same manner as in Example 15 to obtain the final product, [NP(IleOEt)$_{1.49}$(AMPEG750)$_{0.44}$(Aminoethylsulfate)$_{0.07}$]$_n$.

$^1$H NMR Spectrum (CDCl$_3$, ppm):

δ 0.8-1.1 (b, —NHCH(CH(C$\underline{H_3}$)CH$_2$C$\underline{H_3}$)COOCH$_2$CH$_3$), δ 1.1-1.4 (b, —NHCH(CH(CH$_3$)C$\underline{H_2}$CH$_3$)COOCH$_2$C$\underline{H_3}$), δ 1.4-1.8 (b, —NHC$\underline{H}$(C$\underline{H}$(CH$_3$)CH$_2$CH$_3$)COOCH$_2$CH$_3$), δ 2.67-3.2 (b, —NHCH$_2$C$\underline{H_2}$SO$_4$, —NH(CH$_2$CH$_2$O)$_{16}$C$\underline{H_3}$), δ 3.4 (s, —NH(CH$_2$CH$_2$O)$_{16}$C$\underline{H_3}$), δ 3.4-3.9 (b, —NH(C$\underline{H_2}$C$\underline{H_2}$O)$_{16}$CH$_3$, —NHC$\underline{H}$(CH(CH$_3$)CH$_2$CH$_3$)COOC$\underline{H_2}$CH$_3$), δ 3.9-4.3 (b, —NHCH(CH(CH$_3$)CH$_2$CH$_3$)COOC$\underline{H_2}$CH$_3$), Average molecular weight (M$_w$): 8,800

Experimental Example 1: Sol-Gel Transition According to Temperature Change in Phosphazene-Based Polymer Exhibiting Reversible-Irreversible Property Various phosphazene-based polymers, which were prepared according to Examples 1 to 20 and Comparative Examples 1 to 11, were each dissolved in phosphate buffered saline (PBS, pH 7.4) at 4° C. at a concentration of 10 wt %, and the resultants were each placed in an automatic control water tank (TC-501) chamber, and their sol-gel behaviors according to the temperature change were observed. Specifically, each of the resultants was placed in the chamber of a strength meter (Brookfield DB-III Rheometer) equipped with an automatic control tank (TC-501), and the sol-gel behavior according to the temperature change was observed after setting the shear rate at 0.1/sec to 1.7/sec and increasing the temperature at a rate of 0.33° C./minute, and the temperature at which the hydrogel became viscous and the highest strength of the hydrogel were measured. The results are shown in Table 1.

TABLE 1

| Polymer | Structure | State at Low Temperature (4° C.) | Gelation Starting Temperature (° C.) | Maximum Gel Strength (Pa · s) | State at Body Temperature (37° C.) | State After Re-Cooling (10° C.) |
|---|---|---|---|---|---|---|
| Example 1 | [NP(IleOEt)$_{1.19}$(AMPEG550)$_{0.79}$(GlyLacOEt)$_{0.02}$]$_n$ | sol | 12 | 450 | gel | gel |
| Example 2 | [NP(IleOEt)1.56(AMPEG750)0.39(GlyLacOEt)0.05]$_n$ | sol | 17 | 525 | gel | gel |
| Example 3 | [NP(IleOEt)$_{1.77}$(AMPEG1000)$_{0.21}$(GlyLacOEt)$_{0.02}$]$_n$ | sol | 28 | 472 | gel | gel |
| Example 4 | [NP(IleOEt)$_{1.29}$(AMPEG550)$_{0.50}$(Aminoethanol)$_{0.21}$]$_n$ | sol | 18 | 865 | gel | gel |
| Example 5 | [NP(IleOEt)$_{1.45}$(AMPEG750)$_{0.32}$(Aminoethanol)$_{0.23}$]$_n$ | sol | 24 | 306 | gel | gel |
| Example 6 | [NP(IleOEt)$_{1.70}$(AMPEG1000)$_{0.20}$(Aminoethanol)$_{0.10}$]$_n$ | sol | 29 | 468 | gel | gel |
| Example 7 | [NP(IleOEt)$_{1.21}$(AMPEG550)$_{0.61}$(Aminoethylsuccinate)$_{0.18}$]$_n$ | sol | 25 | 412 | gel | gel |
| Example 8 | [NP(IleOEt)$_{1.48}$(AMPEG750)$_{0.33}$(Aminoethylsuccinate)$_{0.19}$]$_n$ | sol | 27 | 450 | gel | gel |
| Example 9 | [NP(IleOEt)$_{1.70}$(AMPEG1000)$_{0.20}$(Aminoethylsuccinate)$_{0.10}$]$_n$ | sol | 18 | 190 | gel | gel |
| Example 10 | [NP(IleOEt)$_{1.23}$(AMPEG550)$_{0.68}$(Aminoethylglutarate)$_{0.09}$]$_n$ | sol | 16 | 256 | gel | gel |
| Example 11 | [NP(IleOEt)$_{1.38}$(AMPEG750)$_{0.38}$(Aminoethylglutarate)$_{0.24}$]$_n$ | sol | 25 | 400 | gel | gel |
| Example 12 | [NP(IleOEt)$_{1.61}$(AMPEG1000)$_{0.22}$(Aminoethylglutarate)$_{0.17}$]$_n$ | sol | 19 | 294 | gel | gel |
| Example 13 | [NP(IleOEt)$_{1.48}$(AMPEG750)$_{0.34}$(Aminoethylglutaric Beta-CD)$_{0.18}$]$_n$ | sol | 15 | 590 | gel | gel |
| Example 14 | [NP(IleOEt)$_{1.51}$(AMPEG750)$_{0.25}$(Aminoethyladipate)$^{0.24}$]$_n$ | sol | 16 | 290 | gel | gel |
| Example 15 | [NP(IleOEt)$_{1.18}$(AMPEG550)$_{0.72}$(Aminoethylsulfate)$_{0.10}$]$_n$ | sol | 20 | 2,545 | gel | gel |
| Example 16 | [NP(IleOEt)$_{1.40}$(AMPEG750)$_{0.30}$(Aminoethylsulfate)$_{0.30}$]$_n$ | sol | 23 | 422 | gel | gel |
| Example 17 | [NP(IleOEt)$_{1.40}$(AMPEG750)$_{0.30}$(AminoethylMethacrylate)$_{0.30}$]$_n$ | sol | 23 | 202 | gel | gel |
| Example 18 | [NP(IleOEt)$_{1.11}$(AMPEG550)$_{0.75}$(Aminoethylacrylate)$_{0.14}$]$_n$ | sol | 17 | 306 | gel | gel |
| Example 19 | [NP(IleOEt)$_{1.55}$(AMPEG750)$_{0.38}$(Aminoethylsuccinate imidazole)$_{0.07}$]$_n$ | sol | 24 | 390 | gel | gel |
| Example 20 | [NP(IleOEt)$_{1.51}$(AMPEG750)$_{0.40}$(Aminoethylsuccinate CRRRRHHHHHGGGGRGDS)$_{0.09}$]$_n$ | sol | 19 | 400 | gel | gel |
| Comparative Example 1 | [NP(IleOEt)$_{1.12}$(AMPEG550)$_{0.85}$(GlyLacOEt)$_{0.03}$]$_n$ | sol | 20 | 205 | gel | sol |
| Comparative Example 2 | [NP(IleOEt)$_{1.32}$(AMPEG750)$_{0.65}$(GlyLacOEt)$_{0.03}$]$_n$ | sol | 34 | 440 | gel | sol |
| Comparative Example 3 | [NP(IleOEt)$_{1.30}$(AMPEG750)$_{0.42}$(Aminoethanol)$_{0.28}$]$_n$ | sol | 28 | 656 | gel | sol |

TABLE 1-continued

| Polymer | Structure | State at Low Temperature (4° C.) | Gelation Starting Temperature (° C.) | Maximum Gel Strength (Pa · s) | State at Body Temperature (37° C.) | State After Re-Cooling (10° C.) |
|---|---|---|---|---|---|---|
| Comparative Example 4 | $[NP(IleOEt)_{1.07}(AMPEG550)_{0.81}(Aminoethylsuccinate)_{0.14}]_n$ | sol | 27 | 112 | gel | sol |
| Comparative Example 5 | $[NP(IleOEt)_{1.39}(AMPEG750)_{0.41}(Aminoethylsuccinate)_{0.20}]_n$ | sol | 28 | 257.5 | gel | sol |
| Comparative Example 6 | $[NP(IleOEt)_{1.05}(AMPEG550)_{0.81}(AminoethylGlutarate)_{0.14}]_n$ | sol | 33 | 468 | gel | sol |
| Comparative Example 7 | $[NP(IleOEt)_{1.32}(AMPEG750)_{0.42}(Aminoethylglutarate)_{0.26}]_n$ | sol | 35 | 175 | gel | sol |
| Comparative Example 8 | $[NP(IleOEt)_{1.61}(AMPEG1000)_{0.34}(Aminoethylglutarate)_{0.05}]_n$ | sol | 56 | 354 | gel | sol |
| Comparative Example 9 | $[NP(IleOEt)_{1.33}(AMPEG750)_{0.47}(Aminoethylglutaric\ beta\text{-}CD)_{0.20}]_n$ | sol | 35 | 360 | gel | sol |
| Comparative Example 10 | $[NP(IleOEt)_{1.48}(AMPEG750)_{0.42}(Aminoethyladipate)_{0.10}]_n$ | sol | 32 | 1,012 | gel | sol |
| Comparative Example 11 | $[NP(IleOEt)_{1.49}(AMPEG750)_{0.44}(Aminoethylsulfate)_{0.07}]_n$ | sol | 30 | 655 | gel | sol |

As shown in Table 1, all of the phosphazene-based polymer solutions (10 wt %) of Examples 1 to 20 and Comparative Examples 1 to 11 were in a state of a flowing solution below the gelation starting temperature, but they were each converted to a gel state when placed at a temperature of 37° C. or above, which is the condition of the body temperature. Then, while the phosphazene-based polymer solutions could still maintain a gel state even when they were cooled again to about 10° C., all of the hydrogels made of the compositions of Comparative Examples 1 to 11 were converted back to a sol state, which is in a state of a flowing solution.

Experimental Example 2: Evaluation of Rheological Property According to Temperature Change in Aqueous Solution of Phosphazene-Based Polymer Exhibiting Reversible-Irreversible Property In order to observe the characteristic of the phosphazene-based polymer solutions of the present invention described above that their reversible sol-gel transition property is lost according to temperature change after they are exposed to a certain temperature or higher, the rheological characteristics of polymer solutions were observed while repeating the temperature change. The results are shown in FIG. 1. The phosphazene-based polymer solutions (10 wt %) of Example 4 and Comparative Example 3 were prepared as in Experimental Example 1. The prepared phosphazene-based polymer solutions of Example 4 and Comparative Example 3 were each applied with a strain of 5% and a frequency of 0.8 Hz, and their storage modulus and loss modulus values according to temperature change were measured. As a result, in the phosphazene-based polymer solution of Example 4, the storage modulus value was lower than the loss modulus value at low temperature, and thus the phosphazene-based polymer solution of Example 4 was present in a solution state, whereas as the temperature increased, the storage modulus value became higher than the loss modulus value thereby forming a hydrogel. In addition, the polymer solution of Example 4 loses its reversible transition property before it reaches 40° C. Accordingly, after the temperature was increased to 40° C., the storage modulus value of the polymer solution of Example 4 was maintained at a significantly higher level than the loss modulus value and its hydrogel state was continuously maintained, even if the temperature was slowly lowered again. In contrast, in the phosphazene-based polymer solution of Comparative Example 3, the storage modulus value was lower than the loss modulus value at low temperature, and thus the phosphazene-based polymer solution of Comparative Example 3 was present in a solution state, whereas as the temperature increased, the storage modulus value became higher than the loss modulus value thereby forming a hydrogel. However, it was confirmed that when the temperature was increased to 40° C. and then slowly lowered again, the hydrogel returned to a solution state according to temperature change as the storage modulus value became lower than the loss modulus value. In addition, it can be seen that when the temperature is slowly increased again and then lowered, the reversible sol-gel transition property due to temperature change is well exhibited.

Figure 2:
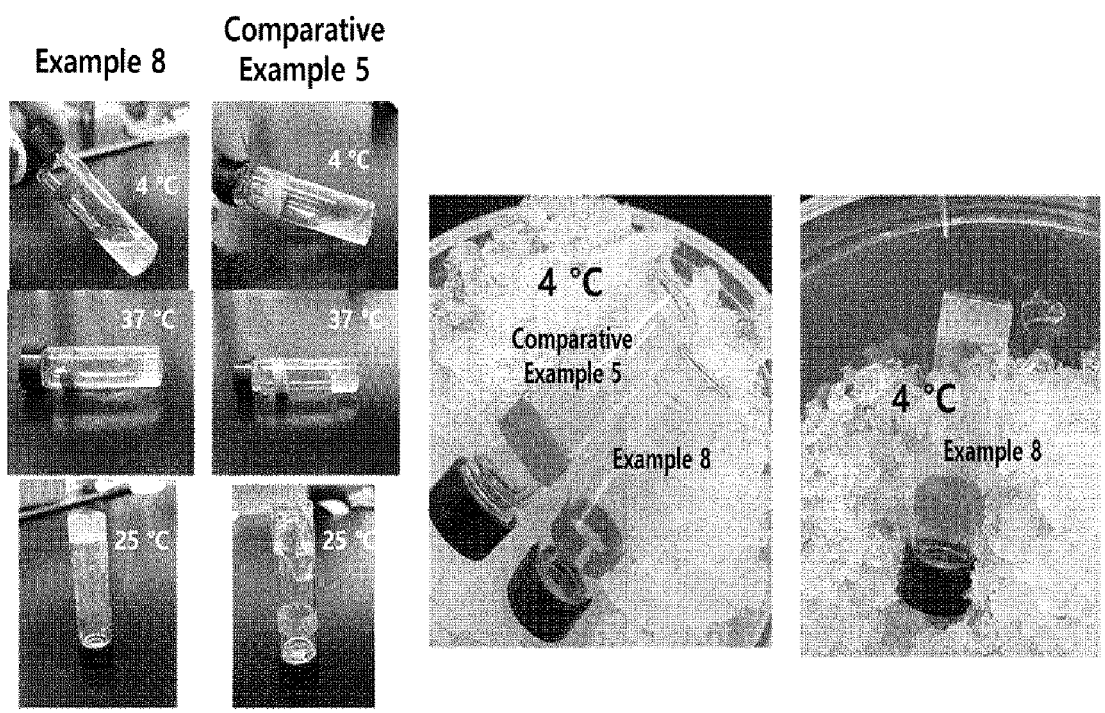
FIG. 2 shows the images illustrating the sol-gel transition according to the temperature of the phosphazene-based polymer solutions according to the Examples and Comparative Examples of the present invention.

Experimental Example 3: Observation of Sol-Gel Transition in Phosphazene-Based Polymer Exhibiting Reversible-Irreversible Property In order to observe, by the naked eye, the characteristic of the phosphazene-based polymer solutions of the present invention described above that their reversible sol-gel transition property is lost according to temperature change after they are exposed to a certain temperature or higher, it was observed whether the phosphazene-based polymer solutions, in a state where they were converted to a hydrogel, could be converted again to a solution state by applying a temperature change therein, and the results are shown in FIG. 2. The phosphazene-based polymer solutions (10 wt %) of Example 8 and Comparative Example 5 were prepared as in Experimental Example 1. Both the phosphazene-based polymer solutions of Example 8 and Comparative Example 5 showed a solution state at 4° C., however, after they were exposed to the body temperature of 37° C. for more than 3 minutes, both solutions showed a hydrogel state in which no flow in the direction of gravity was observed even if the vials were placed upside down. In particular, when the hydrogels, which were formed by the phosphazene-based polymer solutions of Example 8 and Comparative Example 5, were exposed again to 4° C., the hydrogel of Comparative Example 5 was observed to change into a solution state again within 1 minute. However, it was observed that the hydrogel of Example 8 was maintained in the form of a hydrogel without flowing in the direction of gravity even when it was exposed at 4° C. for 6 hours or more.

Experimental Example 4: Use of Phosphazene-Based Polymer Exhibiting Reversible-Irreversible Property for 3D Printing Based on the reversible-irreversible property of the phosphazene-based polymers of the present invention described above, the possibility of their use as a 3D printing ink was confirmed. The phosphazene-based polymer solutions (10 wt %) of Examples 10 and 11 and Comparative Examples 6 and 7 were prepared as in Experimental Example 1. In order to more easily identify the shapes of the resulting products printed in three dimensions, the phosphazene-based polymer solution of Example 11 was mixed with a reddish dye, and the phosphazene-based polymer solution of Comparative Example 7 was mixed with a bluish dye in an amount of less than 0.1% and printed, respectively. In particular, each of the solutions was filled into a 3D printer cartridge in a solution state at 4° C., and it was printed in a range of viscosity at the gelation starting temperature or higher where a weak gel can be formed.

After solidifying the shape of each of the printed products at a temperature where the reversible property may be lost by heating the bottom thereof (e.g., the body temperature of 37° C. in the present invention), they were exposed to room temperature to observe whether their shapes are maintained and/or they have returned to a solution phase.

Figure 3:
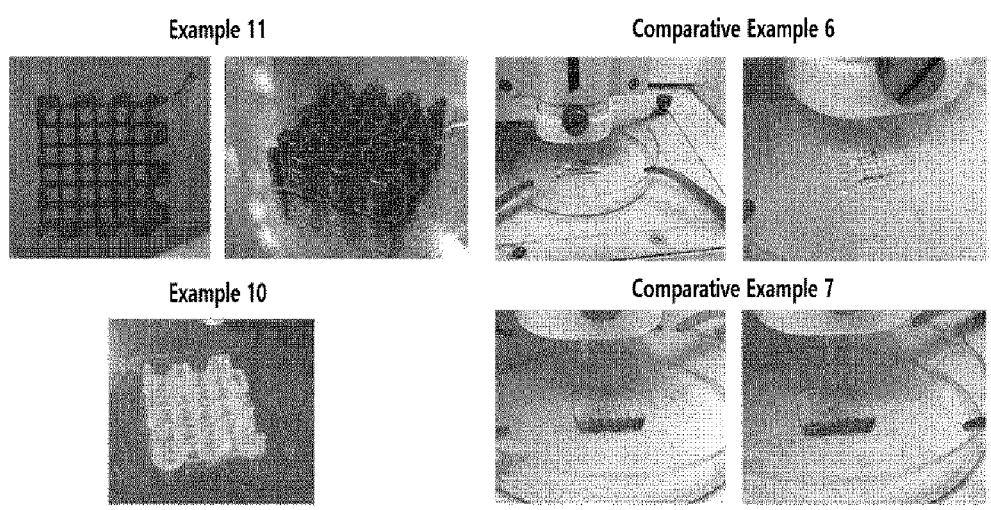
FIG. 3 shows the images illustrating the 3D printed structures prepared by filling with the phosphazene-based polymer solutions according to the Examples and Comparative Examples of the present invention and their shape-retaining abilities according to exposure at room temperature.

In FIG. 3, the structures formed by three-dimensional printing of the phosphazene-based polymer solutions (10 wt %) of Examples 10 and 11 and Comparative Examples 6 and 7 were gelled, and the presence/absence of changes in shape when they were exposed to room temperature are shown in photographs.

It was observed that while the 3D printed structures prepared with the polymer solutions of Examples 10 and 11 maintained their printed 3D shapes without being converted to a solution state even when they were exposed to room temperature after being solidified into hydrogels, the 3D printed structures prepared from the polymer solutions of Comparative Examples 6 and 7 showed a change in their strength of the 3D structures and their shapes collapsed due to a reversible change into a sol state immediately upon their exposure to room temperature after being solidified into hydrogels.

Figure 4:
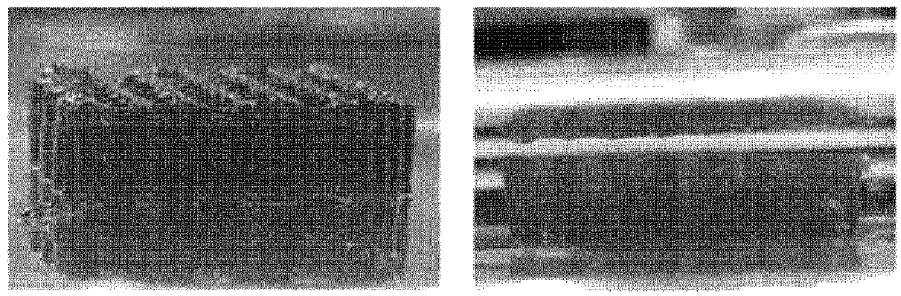
FIG. 4 shows the images illustrating the shape-retaining abilities of the 3D printed structures prepared by filling with the phosphazene-based polymer solutions according to the Examples of the present invention, when the 3D printed structures were immersed into a cell culture medium under the environment where the temperature of the 3D printed structures was not constantly maintained.
Figure 4:
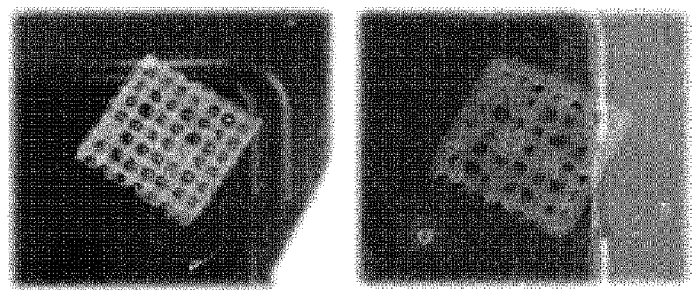
Figure 4:
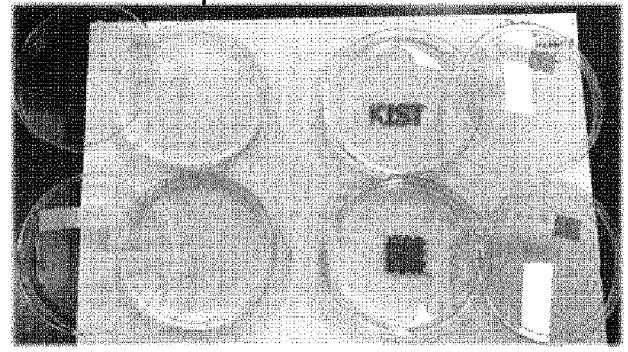

Experimental Example 5: Observation of Shape Maintenance in Phosphazene-Based Polymer Capable of Changing Reversible Property in Cell Culture Medium after 3D Printing In Experimental Example 4, the shape retention ability of the 3D printed products according to temperature change was confirmed. Accordingly, in order to confirm the applicability of the phosphazene-based polymers to 3D culture of cells considering the biocompatibility of the phosphazene-based polymers, the phosphazene-based polymers were exposed to a cell culture medium and thereby their shape retention ability was confirmed. As shown in Experimental Example 4, the structures which were gelled after 3D printing were immersed into a cell culture medium, and the changes in their shape over time were observed. The results are shown in FIG. 4. While the 3D structures prepared using the polymer solutions of Examples 11 and 13 maintained their shapes without the collapse of their structures even if they were immersed into a cell culture medium for a week or longer, the 3D structure prepared using the polymer solution of Comparative Example 7 began to show the changes in strength and/or shapes immediately upon its exposure to room temperature after gelation, and when it was immersed into a cell culture medium, it was immediately dissolved into the cell culture medium and thus its structure collapsed too rapidly to take pictures.

Figure 5:
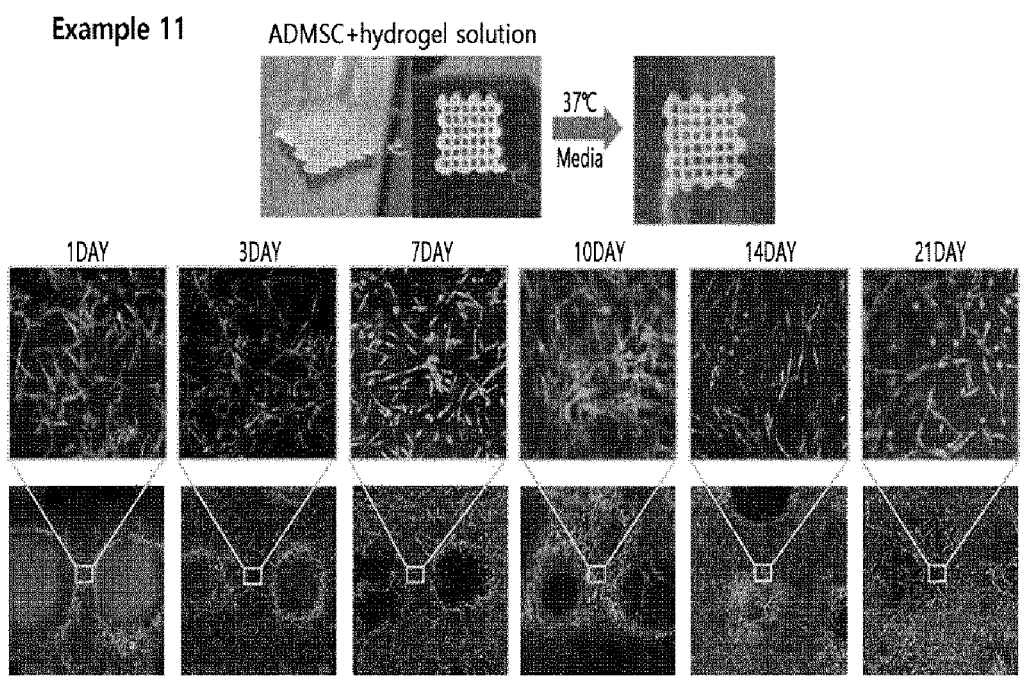
FIG. 5 shows the images illustrating the cell culture and the survival rate according to the culture period of the cells cultured in the 3D printed structures prepared by filling with the phosphazene-based polymer solutions according to the Examples of the present invention, which are mixed with human-derived adipose stem cells under the environment where the temperature of the 3D printed structures was not constantly maintained.

Experimental Example 6: Evaluation of Cell Viability of Phosphazene-Based Polymer Capable of Changing Reversible Property after 3D Printing The applicability of the 3D structures, which were made of the polymer solutions of the Examples whose shape retention ability in a cell culture medium was confirmed through Experimental Example 5, as a cell culture support was confirmed. Specifically, the polymer solution (10 wt %) of Example 11 was prepared, mixed with adipose-derived mesenchymal stem cells (hADMSCs) at 4° C., and then filled in a solution state into a 3D printer cartridge. The resultant was printed in a range of viscosity at the gelation starting temperature or higher where a weak gel can be formed, and the printed shape was solidified by heating the bottom thereof at a temperature where the reversible property may be lost (e.g., 37° C.), and the resultant was immersed into a cell culture medium for 3 weeks, and the viability of the cells contained therein was evaluated. The results are shown in FIG. 5. After immersing ADMSC into the phosphazene-based polymer solution of Example 11, the 3D printed structure was placed in a cell culture medium and was observed while incubating it for 3 weeks, and as a result, it was confirmed that the survival rate of the cells was close to 100% even up to 3 weeks.

Figure 6:
FIG. 6 shows the images illustrating the hydrogels formed by applying the phosphazene-based polymer solutions according to the Examples and Comparative Examples of the present invention to the injured sites exposed to the outside, and the shape-retaining abilities of these formed hydrogels when they were exposed to room temperature.
Figure 6:
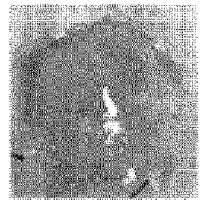
Figure 6:
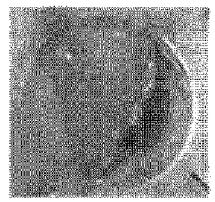
Figure 6:
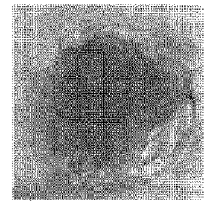

Experimental Example 7: Observation of Presence/Absence of Deformation in Hydrogel Structure Made of Phosphazene-Based Polymer Capable of Changing Reversible Property, when Hydrogel is Transplanted into Exposed Injured Site The applicability of the phosphazene-based polymers of the present invention as an implant for tissue repair or tissue regeneration to injured areas, which are exposed to an external environment where relatively frequent and highly variable changes in temperatures are expected, was confirmed based on the changes in the reversible property and/or drug immersion and release abilities of the phosphazene-based polymer of the present invention. Specifically, hydrogels were formed on the injured areas of 6-week-old male rats with serious damage on its back by treating with the polyphosphazene polymer solutions of Example 13 and Comparative Example 8, respectively, and the maintenance state of the hydrogels was checked at the exposed injured areas. The results are shown in FIG. 6. As shown in FIG. 6, while the shape of the hydrogel made of the polymer solution of Example 13 was maintained for 2 weeks or more, the shape of the hydrogel made of the polymer solution of Comparative Example 8 was not maintained for a long period of time, but was flowed out or absorbed within a day.

Figure 7:
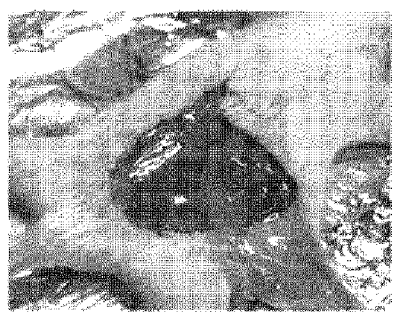
FIG. 7 shows the images illustrating the hydrogels formed by injecting the phosphazene-based polymer solutions according to the Examples and Comparative Examples of the present invention into the body, and the shape-retaining abilities of these formed hydrogels when they were exposed to an external environment.
Figure 7:
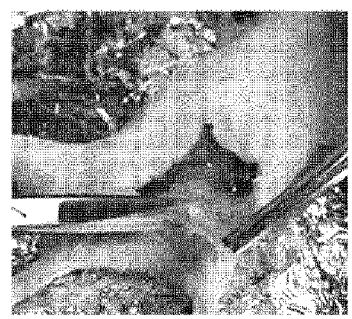
Figure 7:
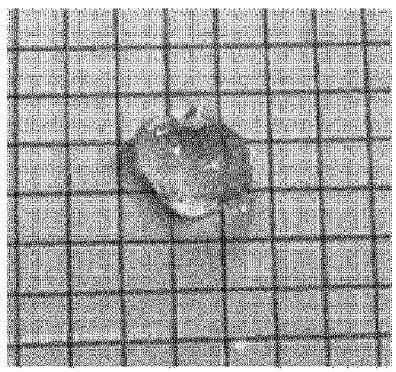
Figure 7:
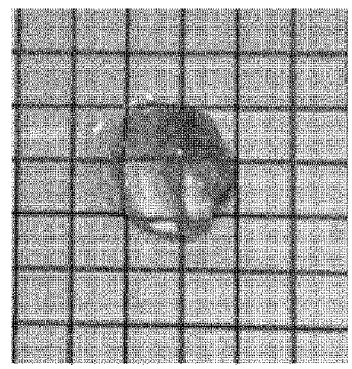

Experimental Example 8: Observation of Presence/Absence of Deformation in Hydrogel Structure Made of Phosphazene-Based Polymer Capable of Changing Reversible Property, when Hydrogel is Exposed to External Environment In order to confirm the potential use of the phosphazene-based polymers of the present invention as a drug delivery system and/or a therapeutic agent for tissue repair or tissue regeneration based on the change in the reversible property of the phosphazene-based polymers of the present invention, the shape retention ability of the hydrogels, which were formed by injection into the body, according to environmental changes was evaluated. Specifically, the polyphosphazene polymer solutions (10 wt %) of Example 11 and Comparative Example 7 were subcutaneously injected to the back areas of 6-week-old male rats to form hydrogels, and the back areas were opened to observe the degradation of the hydrogels after one day, and the immediate state changes therein due to the exposure to an external environment were observed. The results are shown in FIG. 7. As shown in FIG. 7, while the shape of the hydrogel formed by injecting the polymer solution of Example 13 was maintained even when the injected areas were opened and thus it could be easily separated out of the body, the strength of the hydrogel formed by injecting the polymer solution of Comparative Example 7 was weakened upon its exposure to an external environment when the back areas were opened and thus its shape was collapsed, making it difficult to separate the hydrogel out of the body.

Figure 8:
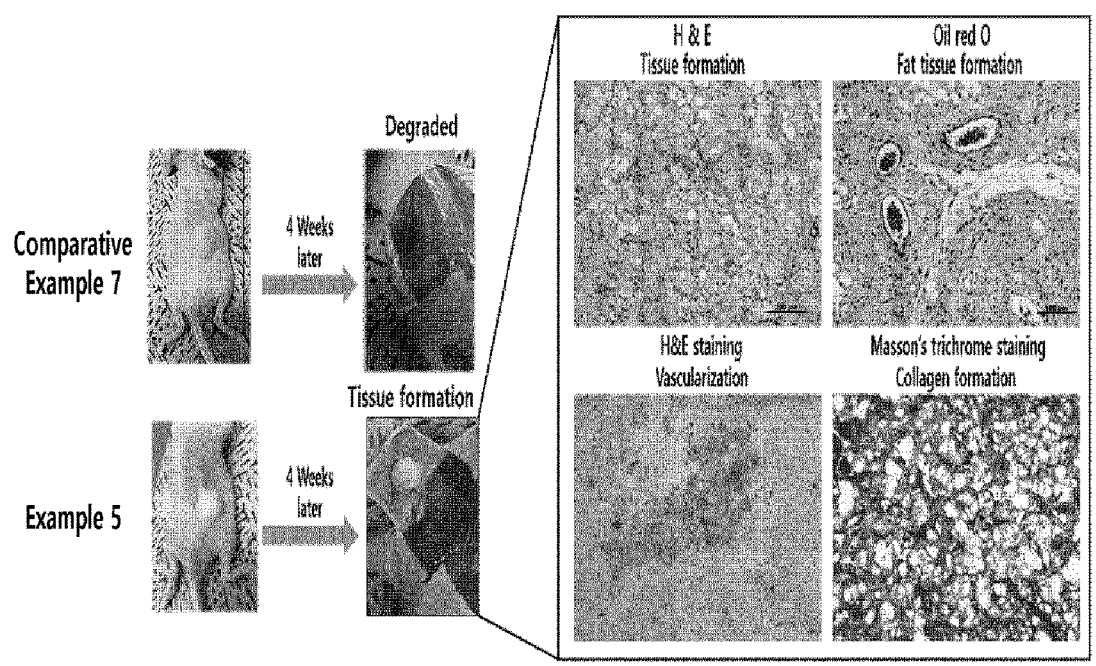
FIG. 8 shows the images illustrating the hydrogels formed by injecting the phosphazene-based polymer solutions according to the Examples and Comparative Examples of the present invention into the body, which formed blood vessels and extracellular matrices due to the neighboring cells introduced after the four-week period and turned into fat tissues.

Experimental Example 9: Observation of Regeneration of Autologous Tissue by Survival after Induction of Cell Invasion and Attachment when Phosphazene-Based Polymer Hydrogel Capable of Changing Reversible Sol-Gel Property is Injected into Body The potential uses of the phosphazene-based polymers of the present invention themselves as a polymer hydrogel for tissue regeneration and as a therapeutic agent for autologous tissue regeneration without the application of any drugs or cells were confirmed based on the changes in the reversible property of the phosphazene-based polymers of the present invention. In a polymer hydrogel, in which the reversible sol-gel transition is altered, its hydrophobic cohesive ability is maintained as the hydrophilic-hydrophobic balance is broken by temperature change, and a state where the hydrophobic property is significantly increased is maintained at a certain temperature or higher. Through such a property, cells introduced into the hydrogel are allowed to be attached to the hydrogel's structural network thereby making their survival easy and the polymer hydrogel is biodegraded and disappears over time; however, the autologous tissues generated by the cells that have been introduced and survived remain at the transplantation site to maintain a certain volume or greater. Specifically, the polyphosphazene polymer solutions (10 wt %) of Example 5 and Comparative Example 7 were subcutaneously injected to the back areas of 6-week-old male rats to form hydrogels, and after 4 weeks, the back areas were cut so as to observe and evaluate the results of degradation of the hydrogels and regeneration of autologous tissues. The results are shown in FIG. 8. As shown in FIG. 8, while the area where a hydrogel was formed by injecting the polymer solution of Comparative Example 7 was completely biodegraded and disappeared after 4 weeks, the area where a hydrogel formed by injecting the polymer solution of Example 5 maintained the shape of a hydrogel form in a volume of more than 80% even after 4 weeks. When the hydrogel area was removed and observed by various staining methods, it was confirmed that the area was replaced with autologous tissue. Hematoxylin & Eosin, Oil red O, and Masson's trichrome staining were used as the staining methods. As a result, it was confirmed that all of the hydrogel-forming areas were filled with cells that had penetrated and were consisted of blood vessels, adipose tissues, and/or extracellular matrices.

Figure 9:
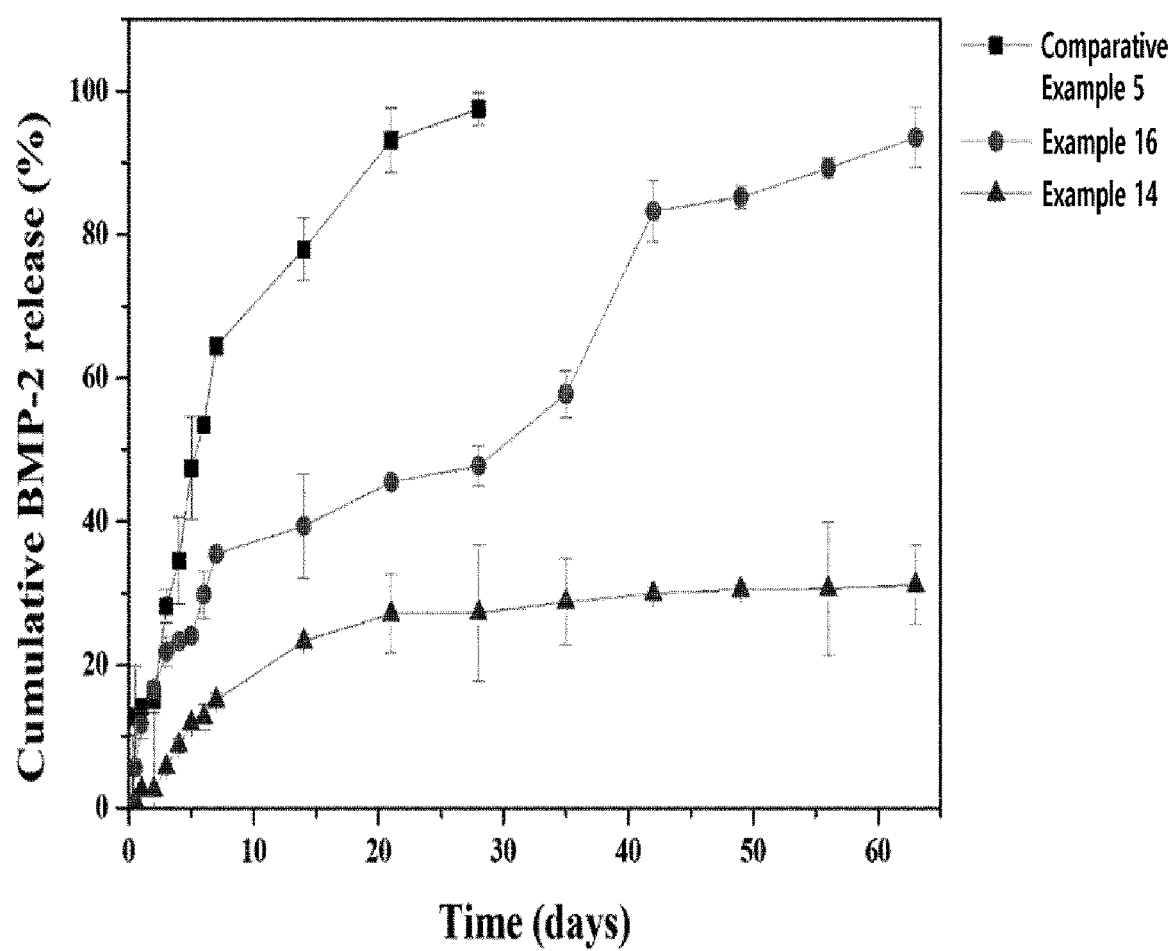
FIG. 9 shows the graph illustrating the amount of bone morphogenetic protein-2 (BMP-2) release measured according to time period in an in vivo environment and in an ex vivo condition similar to an in vivo environment, after forming hydrogels by immersing BMP-2 into the phosphazene-based polymer solutions according to the Examples and Comparative Examples of the present invention.
Figure 10:
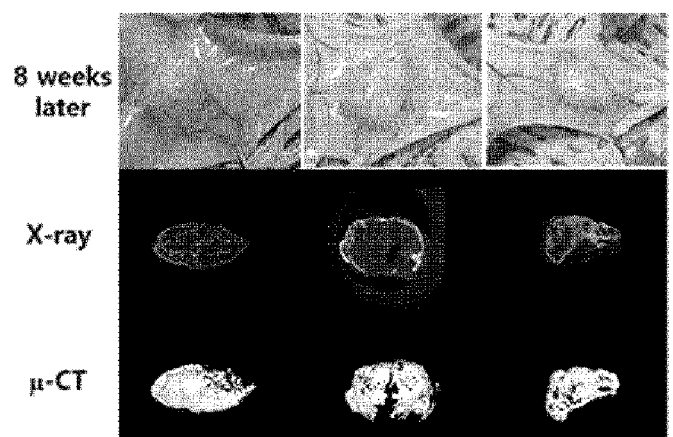
FIG. 10 shows the images illustrating the newly generated bones measured by X-ray and μ-CT, in which the newly generated bones were generated at the hydrogel-forming sites 8 weeks after the phosphazene-based polymer solutions according to the Examples and Comparative Examples of the present invention, into which bone morphogenetic protein-2 (BMP-2) was immersed, were injected into the body.
Figure 10:
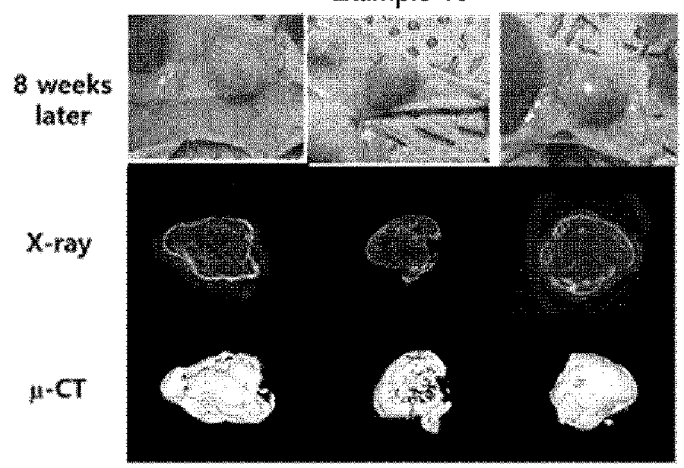
Figure 10:
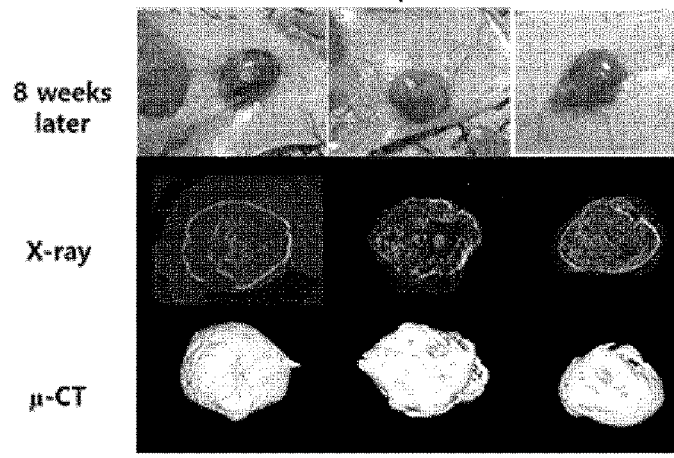

Experimental Example 10: Observation of Abilities of Improved Drug Delivery and Tissue Regeneration of Phosphazene-Based Polymer Hydrogel Capable of Altering Reversible Property The biodegradation time of a hydrogel can be significantly delayed by possessing a property in which the hydrophobic property of a hydrogel is maintained at the maximum level, based on the changes in the reversible property of the phosphazene-based polymers of the present invention, and as a result, it was observed that the delivery period of a drug can be significantly increased. In addition, when the cytokines associated with cell survival and cell differentiation were to be delivered, it was possible to enhance the regeneration ability of tissue to the maximum level by slowly releasing the drug for a long period of time. Specifically, the polyphosphazene polymer solutions (10 wt %) of Comparative Example 5, Example 16, and Example 14 were prepared, and 7 μg each of the same dose of bone morphogenetic protein-2 was added thereto to observe the amount of drug release over a period of time in vitro, subcutaneously injected to the back areas in in vivo conditions (6-week-old male rats) to form hydrogels, and after 8 weeks, the degree of development of newly formed bones was observed. The results are shown in FIGS. 9 and 10, respectively. As shown in FIG. 9, while the bone morphogenetic protein-2 which was released from Comparative Example 5 was released at a rapid rate, the morphogenetic protein-2 which was released from the polymer hydrogels of Example 16 and Example 14 was slowly released over a period of about two months. As shown in FIG. 10, a hydrogel in which morphogenetic protein-2 was included was subcutaneously injected on the back of an animal, and after 8 weeks, the injected hydrogel was separated out of the animal and evaluated to determine whether the injected hydrogel was replaced with bone tissue through X-ray and μ-CT. It was confirmed that when the hydrogel in which morphogenetic protein-2 was included was injected, bone formation was less than 40% of the volume of the injected hydrogel or internal bone formation was poor due to biodegradation of the hydrogel and/or the hydrophilic property of the hydrogel over time, whereas when the polymer hydrogels of Example 16 and Example 14 into each of which morphogenetic protein-2 was immersed were injected, the hydrogels were each replaced with a newly generated bone while maintaining 80% or more of the volume of the first injection even after 8 weeks, due to the phenomena that the hydrogel's biodegradation property is deteriorated and the hydrogel's maximized hydrophobic property is maintained. In addition, it was confirmed that the newly generated bone tissue was well filled with bones to the inside.

The invention claimed is:

1. A composition, comprising:
an aqueous solvent;
a polyphosphazene-based polymer selected from the group consisting of:
poly[(isoleucine ethyl ester)$_{1.45}$(aminomethoxypolyethylene glycol 750)$_{0.32}$(aminoethanol)$_{0.23}$phosphazene]$_n$,
poly[(isoleucine ethyl ester)$_{1.70}$(aminomethoxypolyethylene glycol 1000)$_{0.20}$(aminoethanol)$_{0.10}$phosphazene]$_n$,
poly[(isoleucine ethyl ester)$_{1.48}$(aminomethoxypolyethylene glycol 750)$_{0.33}$(aminoethylsuccinate)$_{0.19}$phosphazene]$_n$, poly[(isoleucine ethyl ester)$_{1.70}$(aminomethoxypolyethylene glycol 1000)$_{0.20}$(aminoethylsuccinate)$_{0.10}$phosphazene]$_n$, poly[(isoleucine ethyl ester)$_{1.38}$(aminomethoxypolyethylene glycol 750)$_{0.38}$(aminoethylglutarate)$_{0.24}$phosphazene]$_n$, poly[(isoleucine ethyl ester)$_{1.61}$(aminomethoxypolyethylene glycol 1000)$_{0.22}$(aminoethylglutarate)$_{0.17}$phosphazene]$_n$, poly[(isoleucine ethyl ester)$_{1.48}$(aminomethoxypolyethylene glycol 750)$_{0.34}$(aminoethylglutaratebeta-cyclodextrin)$_{0.18}$phosphazene]$_n$, poly[(isoleucine ethyl ester)$_{1.51}$(aminomethoxypolyethylene glycol 750)$_{0.25}$(aminoethyladipate)$_{0.24}$phosphazene]$_n$, poly[(isoleucine ethyl ester)$_{1.40}$(aminomethoxypolyethylene glycol 750)$_{0.30}$(aminoethylsulfate)$_{0.30}$phosphazene]$_n$, poly[(isoleucine ethyl ester)$_{1.40}$(aminomethoxypolyethylene glycol 750)$_{0.30}$(aminoethylmethacrylate)$_{0.30}$phosphazene]$_n$, poly[(isoleucine ethyl ester)$_{1.55}$(aminomethoxypolyethylene glycol 750)$_{0.38}$(aminoethylsuccinateimidazole)$_{0.07}$phosphazene]$_n$, and poly[(isoleucine ethyl ester)$_{1.51}$(aminomethoxypolyethylene glycol 750)$_{0.40}$(aminoethylsuccinateCRRRRHHHHHGGGGGRGDS)$_{0.09}$phosphazene]$_n$, wherein n is an integer of 3 to 100,000, wherein "CRRRRHHHHHGGGGGRGDS" of the poly[(isoleucine ethyl ester)$_{1.51}$(aminomethoxypolyethylene glycol 750)$_{0.40}$(aminoethylsuccinateCRRRRHHHHHGGGGGRGDS)$_{0.09}$phosphazene]$_n$ is an amino acid sequence.

2. The composition of claim 1, wherein the polyphosphazene-based polymer is poly[(isoleucine ethyl ester)$_{1.45}$(aminomethoxypolyethylene glycol 750)$_{0.32}$(aminoethanol)$_{0.23}$phosphazene]$_n$.

3. The composition of claim 1, wherein the polyphosphazene-based polymer is poly[(isoleucine ethyl ester)$_{1.70}$(aminomethoxypolyethylene glycol 1000)$_{0.20}$(aminoethanol)$_{0.10}$phosphazene]$_n$.

4. The composition of claim 1, wherein the polyphosphazene-based polymer is poly[(isoleucine ethyl ester)$_{1.48}$(aminomethoxypolyethylene glycol 750)$_{0.33}$(aminoethylsuccinate)$_{0.19}$phosphazene]$_n$.

5. The composition of claim 1, wherein the polyphosphazene-based polymer is poly[(isoleucine ethyl ester)$_{1.70}$(aminomethoxypolyethylene glycol 1000)$_{0.20}$(aminoethylsuccinate)$_{0.10}$phosphazene]$_n$.

6. The composition of claim 1, wherein the polyphosphazene-based polymer is poly[(isoleucine ethyl ester)$_{1.38}$(aminomethoxypolyethylene glycol 750)$_{0.38}$(aminoethylglutarate)$_{0.24}$phosphazene]$_n$.

7. The composition of claim 1, wherein the polyphosphazene-based polymer is poly[(isoleucine ethyl ester)$_{1.61}$(aminomethoxypolyethylene glycol 1000)$_{0.22}$(aminoethylglutarate)$_{0.17}$phosphazene]$_n$.

8. The composition of claim 1, wherein the polyphosphazene-based polymer is poly[(isoleucine ethyl ester)$_{1.48}$(aminomethoxypolyethylene glycol 750)$_{0.34}$(aminoethylglutarate beta-cyclodextrin)$_{0.18}$phosphazene]$_n$.

9. The composition of claim 1, wherein the polyphosphazene-based polymer is poly[(isoleucine ethyl ester)$_{1.51}$(aminomethoxypolyethylene glycol 750)$_{0.25}$(aminoethyladipate)$_{0.24}$phosphazene]$_n$.

10. The composition of claim 1, wherein the polyphosphazene-based polymer is poly[(isoleucine ethyl ester)$_{1.40}$(aminomethoxypolyethylene glycol 750)$_{0.30}$(aminoethylsulfate)$_{0.30}$phosphazene]$_n$.

11. The composition of claim 1, wherein the polyphosphazene-based polymer is poly[(isoleucine ethyl ester)$_{1.40}$(aminomethoxypolyethylene glycol 750)$_{0.30}$(aminoethyl-Methacrylate)$_{0.30}$phosphazene]$_n$.

12. The composition of claim 1, wherein the polyphosphazene-based polymer is poly[(isoleucine ethyl ester)$_{1.55}$(aminomethoxypolyethylene glycol 750)$_{0.38}$(aminoethylsuccinateimidazole)$_{0.07}$phosphazene]$_n$.

13. The composition of claim 1, wherein the polyphosphazene-based polymer is poly[(isoleucine ethyl ester)$_{1.51}$(aminomethoxypolyethylene glycol 750)$_{0.40}$(aminoethylsuccinateCRRRRHHHHHGGGGGRGDS)$_{0.09}$phosphazene]$_n$.

14. The composition of claim 1, further comprising at least one selected from the group consisting of a drug, cells, nanoparticles, and microparticles.

* * * * *